United States Patent
Carron et al.

(10) Patent No.: US 8,834,159 B2
(45) Date of Patent: Sep. 16, 2014

(54) ADJUSTABLE ANGLE PROPHY ANGLE ADAPTER

(75) Inventors: Chris J. Carron, Bloomsdale, MO (US); David G. Grither, Ste. Genevieve, MO (US)

(73) Assignee: Angstrom Manufacturing, Inc., Bloomsdale, MO (US)

( * ) Notice: Subject to any disclaimer, the term of this patent is extended or adjusted under 35 U.S.C. 154(b) by 192 days.

(21) Appl. No.: 12/712,993

(22) Filed: Feb. 25, 2010

(65) Prior Publication Data

US 2010/0196846 A1 Aug. 5, 2010

Related U.S. Application Data

(63) Continuation-in-part of application No. 12/503,151, filed on Jul. 15, 2009, now abandoned, which is a continuation-in-part of application No. 11/862,628, filed on Sep. 27, 2007, now Pat. No. 8,123,523, which is a continuation-in-part of application No. 11/682,927, filed on Mar. 7, 2007, now abandoned, which is a continuation-in-part of application No. 11/189,193, filed on Jul. 26, 2005, now Pat. No. 7,422,433.

(51) Int. Cl.
| | |
|---|---|
| *A61C 1/12* | (2006.01) |
| *A61C 1/16* | (2006.01) |
| *A61C 17/26* | (2006.01) |
| *A61C 1/18* | (2006.01) |
| *A61C 17/00* | (2006.01) |

(52) U.S. Cl.
CPC .............. *A61C 1/12* (2013.01); *A61C 17/005* (2013.01); *A61C 1/185* (2013.01)
USPC ............................. 433/116; 433/130; 433/133

(58) Field of Classification Search
USPC ......... 433/103, 108, 109, 112, 114, 116, 124, 433/125, 126, 130, 131, 133; 606/78–83, 606/167; 464/171, 173; 81/57.13, 57.29
See application file for complete search history.

(56) References Cited

U.S. PATENT DOCUMENTS

| | | | | | |
|---|---|---|---|---|---|
| 219,849 | A | * | 9/1879 | Cushing | 433/130 |
| 374,286 | A | * | 12/1887 | Bell et al. | 433/130 |
| 597,469 | A | * | 1/1898 | Marshall | 433/124 |
| 600,243 | A | * | 3/1898 | Shaw | 433/130 |
| 606,755 | A | * | 7/1898 | Browne | 433/112 |
| 623,469 | A | | 4/1899 | Hailer | |
| 636,476 | A | * | 11/1899 | Webster | 433/130 |
| 647,010 | A | * | 4/1900 | Marshall | 433/130 |

(Continued)

*Primary Examiner* — Todd Manahan
*Assistant Examiner* — Michael R Ballinger
(74) *Attorney, Agent, or Firm* — Steven M. Greenberg, Esq.; Kara A. Brotman, Esq.; CRGO Law

(57) ABSTRACT

An adjustable angle adapter for a prophy angle comprises a nose, a rotating member, a body, a shaft, a multi-axis rotation joint, and an outer joint. The nose is configured to receive a portion of the prophy angle. The rotating member is positioned within the nose. The body is adjustably connected to the nose. The shaft is positioned within the body. The multi-axis rotation joint connects the shaft to the rotating member. The outer joint includes a ball portion connected to one of the body and the nose, and a ball receiver connected to an other of the body and the nose. The nose is configured to pivot relative to the body into at least a first configuration and a second configuration.

11 Claims, 18 Drawing Sheets

(56) References Cited

U.S. PATENT DOCUMENTS

| | | | |
|---|---|---|---|
| 886,862 A * | 5/1908 | Repsold | 433/117 |
| 949,273 A * | 2/1910 | Hinrichsen | 433/116 |
| 1,035,239 A * | 8/1912 | Rosenthal | 279/42 |
| 1,051,025 A * | 1/1913 | Spicer | 464/122 |
| 1,170,524 A | 2/1916 | Fernald | |
| 1,316,685 A * | 9/1919 | Cates | 433/123 |
| 1,333,809 A | 3/1920 | Laurer et al. | |
| 1,379,880 A | 5/1921 | Seaborn | |
| 1,485,963 A * | 3/1924 | Curry | 433/116 |
| 1,688,136 A | 10/1928 | Chayes et al. | |
| 1,688,410 A * | 10/1928 | Chayes et al. | 279/76 |
| 1,999,488 A | 4/1935 | Swisher et al. | |
| 2,025,779 A | 12/1935 | Roelke | |
| 2,201,190 A * | 5/1940 | Mastrud | 15/22.4 |
| 2,372,731 A * | 4/1945 | Gresham et al. | 74/44 |
| 2,400,912 A | 5/1946 | Britt et al. | |
| 2,439,262 A * | 4/1948 | Gresham et al. | 62/414 |
| 2,648,787 A * | 8/1953 | Smithson, Jr. | 310/47 |
| 2,749,567 A * | 6/1956 | Krueger | 15/172 |
| 3,101,542 A * | 8/1963 | Fodor | 433/105 |
| 3,423,068 A * | 1/1969 | Hall | 415/151 |
| 3,509,629 A | 5/1970 | Kidokoro et al. | |
| 3,939,599 A * | 2/1976 | Henry et al. | 433/99 |
| 4,008,521 A * | 2/1977 | Epstein et al. | 433/123 |
| 4,278,429 A * | 7/1981 | Straihammer et al. | 433/126 |
| 4,281,989 A * | 8/1981 | Glover et al. | 433/130 |
| RE31,537 E * | 3/1984 | Flatland | 433/82 |
| 4,827,552 A * | 5/1989 | Bojar et al. | 15/28 |
| 4,989,287 A * | 2/1991 | Scherer | 15/22.1 |
| 5,020,281 A * | 6/1991 | Neff | 451/358 |
| 5,433,605 A | 7/1995 | Strobl, Jr. | |
| 5,490,781 A * | 2/1996 | Wade | 433/116 |
| 5,575,647 A * | 11/1996 | Grubbs | 433/114 |
| 6,050,989 A * | 4/2000 | Fox et al. | 606/1 |
| 6,651,347 B2 * | 11/2003 | Uhl | 30/383 |
| 6,928,902 B1 * | 8/2005 | Eyssallenne | 81/57.26 |
| 7,029,274 B1 * | 4/2006 | Capps | 433/1 |
| 7,101,176 B1 * | 9/2006 | Capps | 433/1 |
| 2005/0144744 A1 * | 7/2005 | Thiess et al. | 15/22.1 |

\* cited by examiner

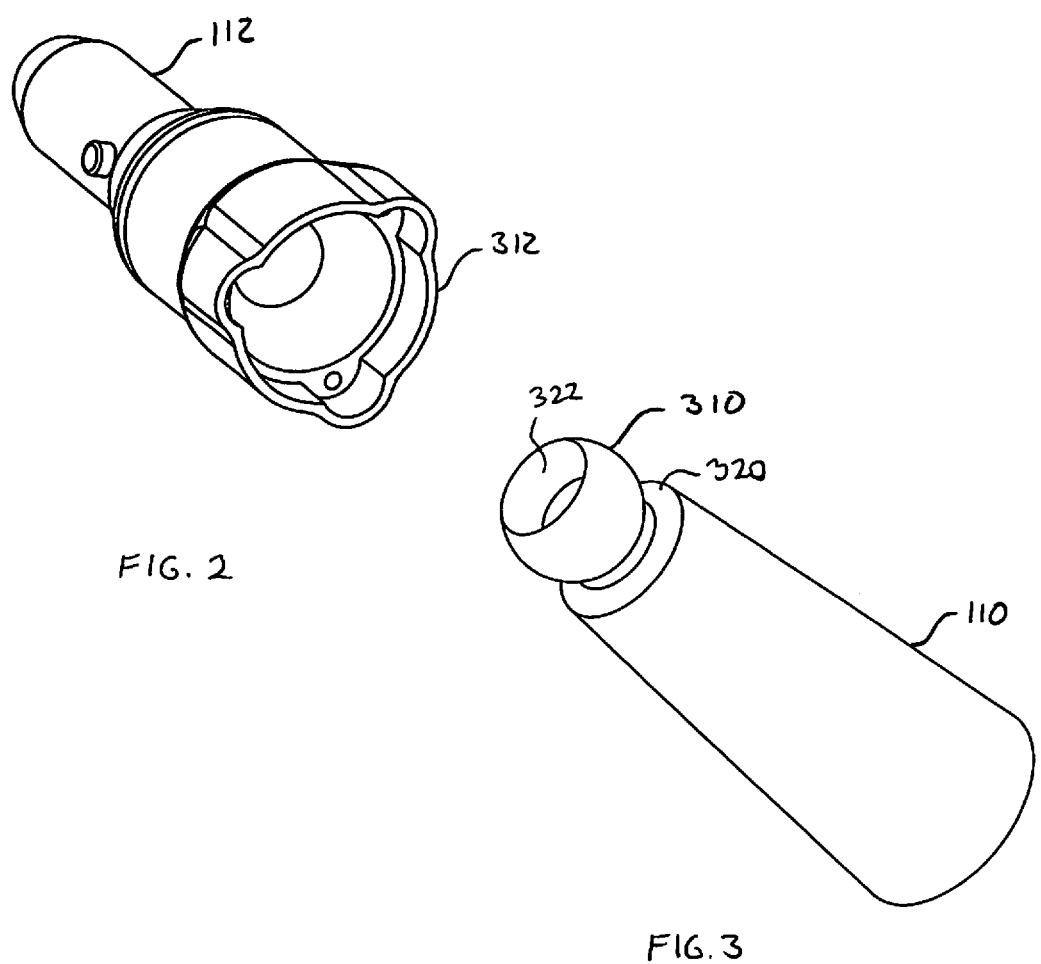

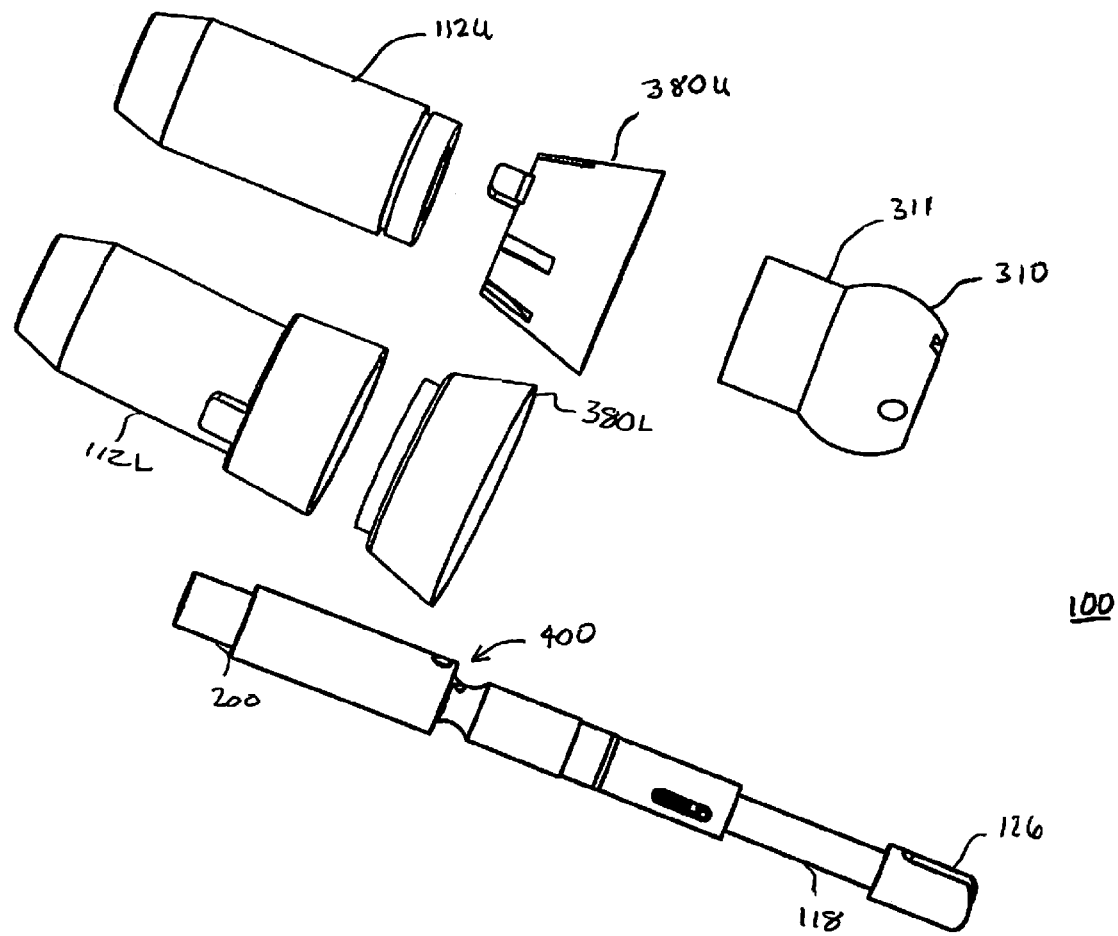
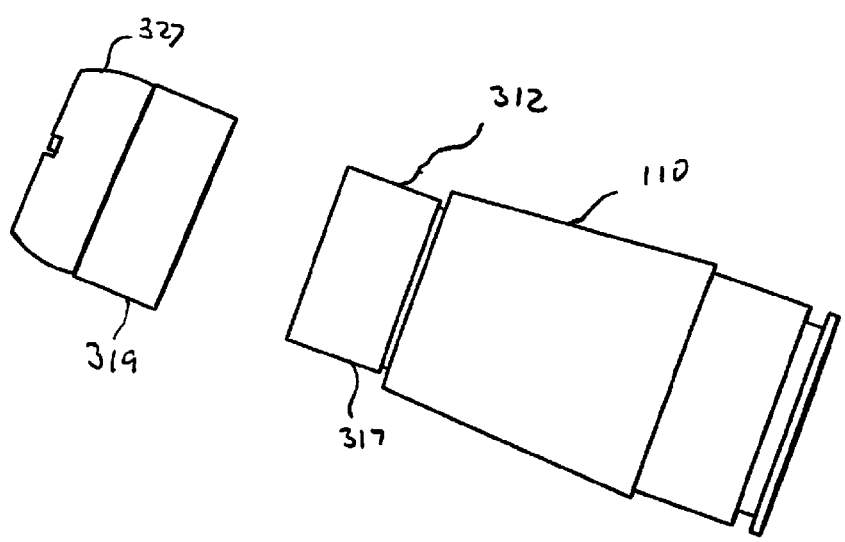
FIG. 7

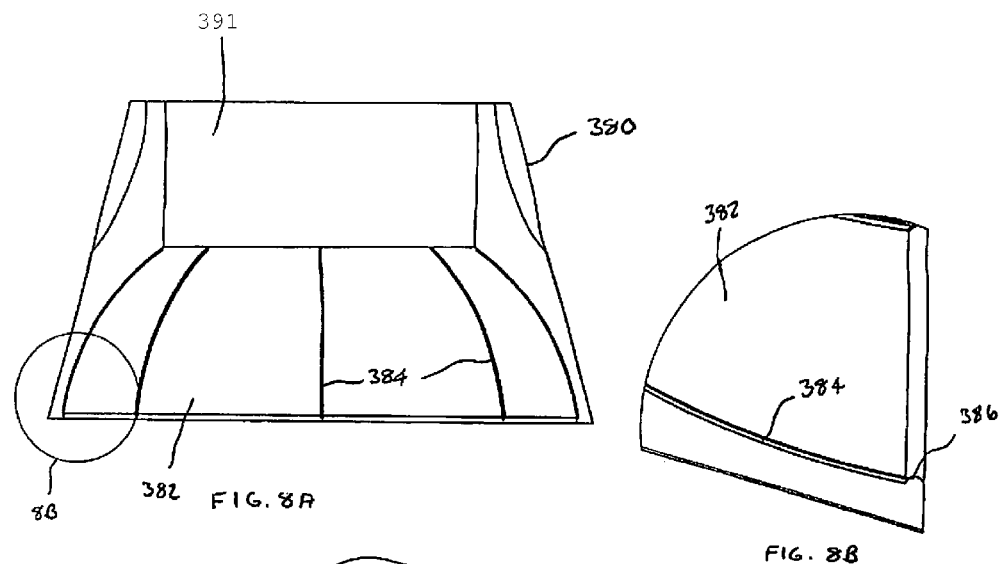
FIG. 8A
FIG. 8B
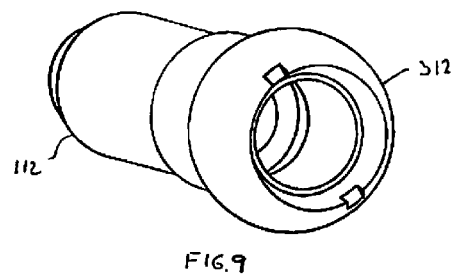
FIG. 9
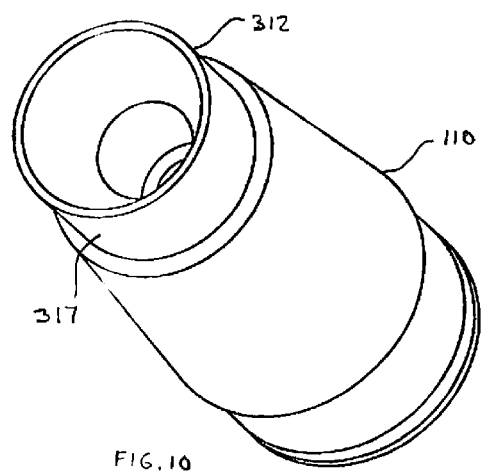
FIG. 10

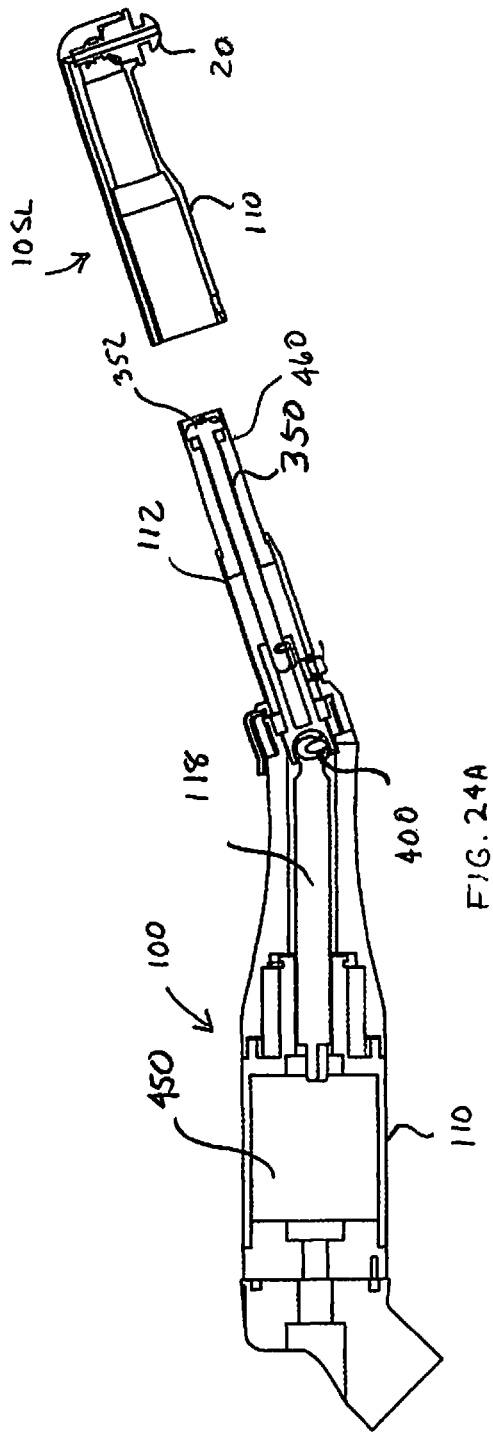
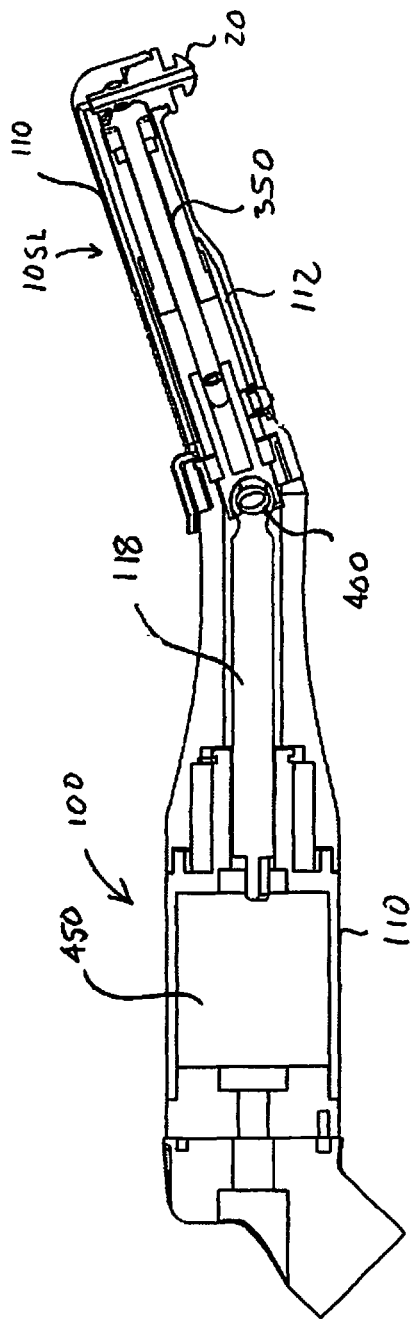
FIG. 24A
FIG. 24B

ADJUSTABLE ANGLE PROPHY ANGLE ADAPTER

CROSS-REFERENCE TO RELATED APPLICATIONS

This application is a Continuation-In-Part of U.S. application Ser. No. 12/503,151, filed on Jul. 15, 2009 now abandoned, which is a Continuation-In-Part of U.S. application Ser. No. 11/862,628, filed on Sep. 27, 2007 now U.S. Pat. No. 8,123,523, which is a Continuation-In-Part of U.S. application Ser. No. 11/682,927, filed on Mar. 7, 2007 now abandoned, which is a Continuation-In-Part of U.S. application Ser. No. 11/189,193, filed on Jul. 26, 2005 now U.S. Pat. No. 7,422,433, all of which are incorporated herein by reference in their entirety. This application is related to U.S. application Ser. No. 12/713,088, filed on Feb. 25, 2010, entitled "PROPHY ANGLE AND ADAPTER WITH GUARD," and U.S. application Ser. No. 12/713,070, filed on Feb. 25, 2010, now U.S. Pat. No. 8,459,992, entitled "PROPHY ANGLE AND ADAPTER WITH LATCH," all of which are incorporated herein by reference in their entirety.

BACKGROUND OF THE INVENTION

1. Field of the Invention

The disclosure relates generally to dental instruments and, more specifically, to adapters for use with prophy angles.

2. Description of the Related Art

Dental prophylaxis angles, generally referred to as "prophy angles," are commonly used dental instruments for providing rotation for dental tools such as brushes, prophy cups, or other receptacles used in cleaning/polishing teeth. Referring to FIGS. 22 and 23, a prophy angle 10 typically includes a housing 16 having a neck 18 and a head portion 14 extending at approximately a 90° angle to the neck 18, which increases the ability of a dentist to reach various surfaces of the teeth of a patient. A drive shaft or prophy rotating member 12 can be located within the housing 16 and attached to a driven gear 20 in the head of the prophy angle. Prophy angles 10 are generally affixed to an adapter or hand piece (not shown), which connects the prophy angle to a drive source (not shown), thereby enabling a rotating motion of the prophy rotating member 12 and driven gear 20 of the prophy angle and any affixed dental tool.

Prophy angles 10 are commonly manufactured from lightweight plastic to make them disposable, thereby increasing overall sterility in the dental environment. An issue associated with making the prophy angles 10, and their constituent elements, such as the prophy rotating member 12, from plastic is the ability of the hand piece to engage the prophy rotating member 12 without slipping and to engage the prophy rotating member 12 without excessive damage to the prophy rotating member 12. Another issue associated with the use of prophy angles 10 is the widespread use of many different and incompatible types of couplings between the drive source and the hand piece and between the hand piece and the prophy angle 10. Yet another issue associated with the use of prophy angles 10 is the number of adapters needed to provide different orientations.

BRIEF SUMMARY OF THE INVENTION

An adjustable angle adapter for a prophy angle comprises a nose, a rotating member, a body, a shaft, a multi-axis rotation joint, and an outer joint. The nose is configured to receive a portion of the prophy angle. The rotating member is positioned within the nose. The body is adjustably connected to the nose. The shaft is positioned within the body. The multi-axis rotation joint connects the shaft to the rotating member. The outer joint includes a ball portion connected to one of the body and the nose, and a ball receiver connected to an other of the body and the nose. The nose is configured to pivot relative to the body into at least a first configuration and a second configuration In additional aspects of the adapter, in the first configuration, the body and the nose share a common centerline. Also, in the second configuration, a centerline of the body is at a non-zero degree angle to a centerline of the nose. The multi-axis rotation joint and the outer joint pivot about a common pivot point. The nose is configured to pivot relative to the body from between zero degrees to about eighteen degrees. A plurality of drag devices are disposed between the ball portion and the ball receiver. Additionally, the adapter includes a motor integral with the body.

In a further aspect, the ball portion is connected to the body, and the ball receiver connected to the nose. Additionally, the adapter includes a lock removably attachable to the ball receiver, and the ball portion is positioned between the ball receiver and the lock.

In yet another aspect, the ball portion is connected to the nose, and the ball receiver is connected to the body. The adapter includes a guard removably attachable to the nose. The guard includes an inner surface having a radius that substantially matches a radius of an outer surface of the ball receiver.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein:

FIG. 2 is a perspective view of a ball receiver and nose of the adjustable angle adapter, in accordance with the inventive arrangement;

FIG. 3 is a perspective view of a ball portion and body of the adjustable angle adapter, in accordance with the inventive arrangement;

FIGS. 7 and 7A are exploded views of an adjustable angle adapter, in accordance with different embodiments of the inventive arrangement;

FIGS. 8A and 8B are, respectively, a side and detail view of a guard, in accordance with the inventive arrangement;

FIG. 9 is a perspective view of a ball portion and nose of the adjustable angle adapter, in accordance with the inventive arrangement;

FIG. 10 is a perspective view of a ball receiver and body of the adjustable angle adapter, in accordance with the inventive arrangement;

FIGS. 24A and 24B are, respectively, exploded and assembled cross-sectional views of a shaft-less prophy angle and adapter.

DETAILED DESCRIPTION OF THE INVENTION

Figure 1:
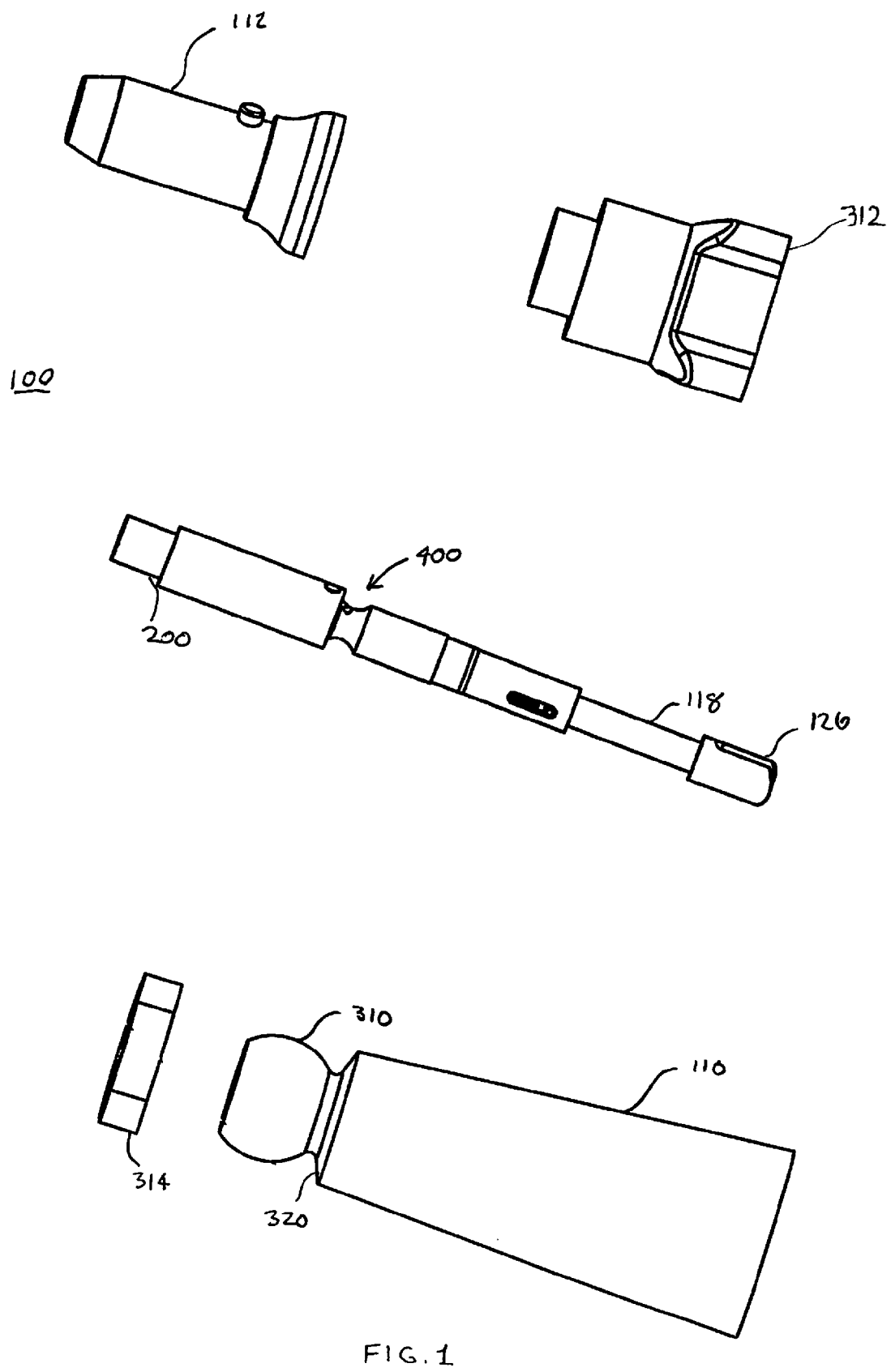
FIG. 1 is an exploded, side view of an adjustable angle adapter, in accordance with the inventive arrangement.

FIGS. 1, 4, and 6A-6B illustrate an exemplar adjustable angle adapter 100 for use with a prophy angle 10. The adapter 100 includes a body 110 and a nose 112. The adapter 100 includes a shaft 118, which is adjustably connected to a nose rotating member, such as a collet 200, for receiving a prophy rotating member 12 of the prophy angle 10. The nose 112 includes a first bore 114 for receiving the prophy rotating member 12 and, in certain configurations, a portion of the shaft 118 and/or collet 200. In certain aspects, the adapter 100 includes a multi-axis rotation joint 400 that connects the shaft 118 to the nose rotating member (e.g., collet 200). Additionally, the adapter 100 includes an outer joint 300 that connects the body 110 to the nose 112.

In certain configurations, the outer joint 300 permits the nose 112 to pivot relative to the body 110 (or the body 110 to pivot relative to the nose 112). As referred to herein, the pivoting is about a pivot point at the intersection of a centerline of the body 110 and a centerline of the nose 112. The centerline of the body 110 and the centerline of the nose 112 substantially correspond, respectively, to a rotational axis $RA_2$ of the shaft 118 and the rotational axis $RA_1$ of the nose rotating member (e.g., collet 200). As referred to herein, "to pivot" is defined as a change in the angle between the rotational axis $RA_2$ (or centerline of the body 110) of the shaft 118 and the rotational axis $RA_1$ (or centerline of the nose 112) of the nose rotating member (e.g., collet 200).

The outer joint 300 can also permit the nose 112 to rotate relative to the body (or the body 110 to rotate relative to the nose 112). As the term is used herein, the rotation of the nose 112 and/or body 110 refers to the rotation of the nose 112 and/or body 110 about its own centerline/pivot axis. Additionally, the outer joint 300 can permit the nose 112 to both rotate and pivot relative to the body (or the body 110 to rotate relative to the nose 112).

Figure 4:
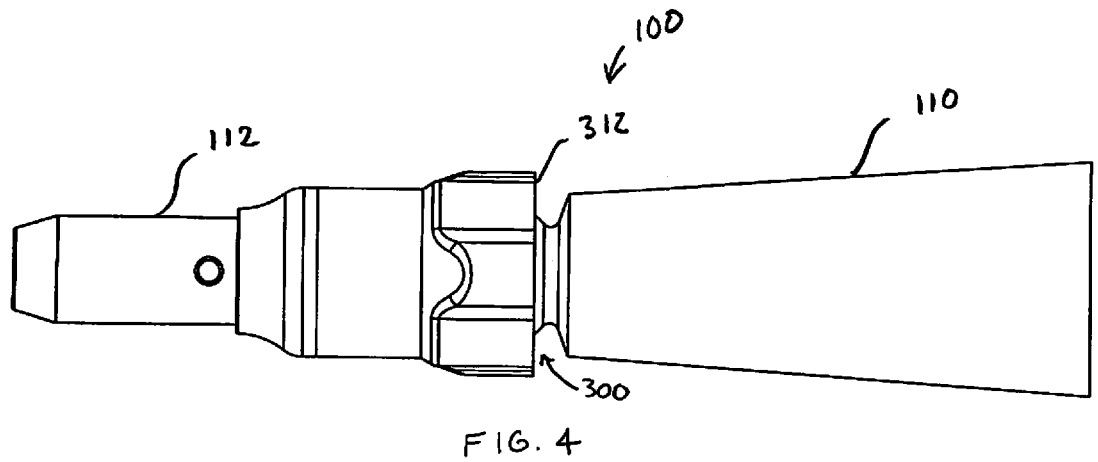
FIG. 4 is a side view of the adjustable angle adapter.
Figure 6A:
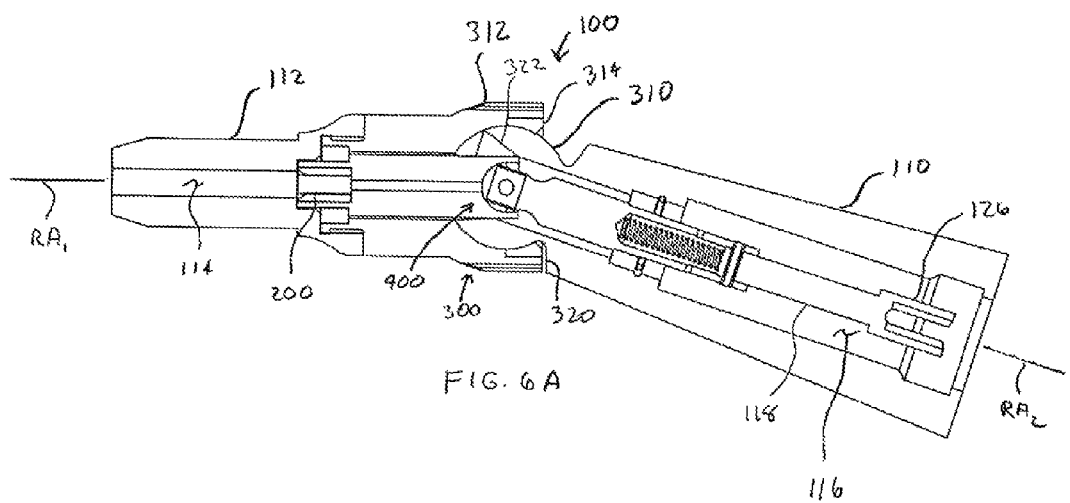
FIGS. 6A and 6B are side cross-sectional views of the adjustable angle adapter, respectively, in straight and contrastyle orientations.
Figure 6B:
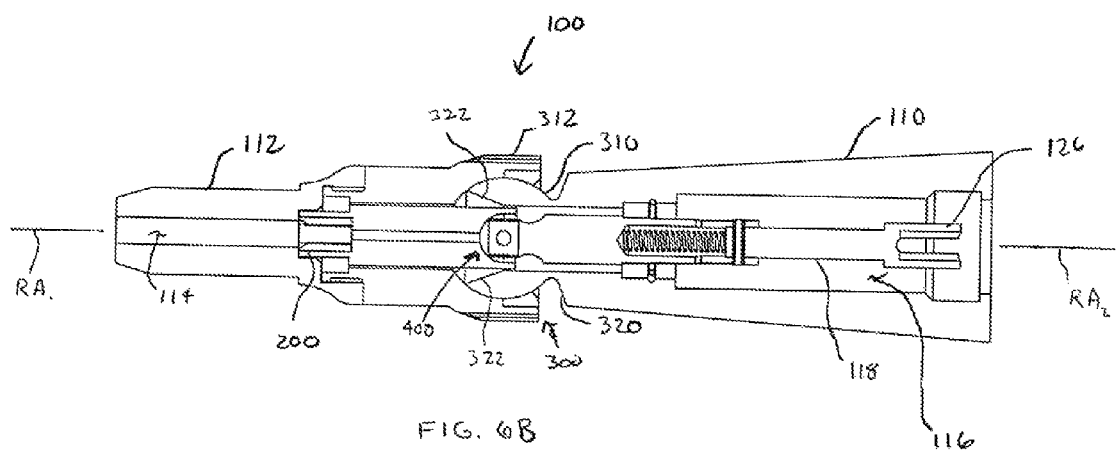

The adapter 100 can be adjusted from a configuration in which the nose 112 and body 110 share a common centerline (also referred to as a straight adapter), as illustrated in FIGS. 4 and 6B, to a configuration in which the centerlines of the nose 112 and the body 110 are at a non-zero degree angle to one another (also referred to as a contra-style or angled adapter), as illustrated in FIG. 6A. Although not limited in this manner, in certain aspects of the adapter, the multi axis rotation joint 400 and the outer joint 300 pivot about a common pivot point.

In certain aspects of the adapter 100, the outer joint 300 permits the nose 112 to pivot relative to the body 110 by at least 18 degrees. Additionally, the outer joint 300 permits the nose 112 to pivot relative to body 110 to multiple different angles between a straight configuration (i.e., 0 degrees) and a maximum-angle configuration (e.g., 18 degrees). In this manner, the adjustable angle adapter 100 provides greater flexibility to a user of the adapter 100. Advantageously, this flexibility can reduce the number of different types of adapters 100 a particular user may require. In certain aspects, the maximum-angle configuration can be as high as 30 degrees.

Although not limited in this manner, a contra-style adapter 100 is used in dentistry to obtain better access to the back teeth of a patient. Thus, whereas prior adapters were limited to a single configuration, the adjustable angle adapter 100 can provide two or more different configurations. As will be discussed in greater detail below, many mechanisms by which the nose 112 pivot relative to the body 110 are acceptable for use with the present adjustable angle adapter 100. Additionally, although the currently illustrated adapter 100 includes a single joint, multiple joints can be provided.

Figure 5:
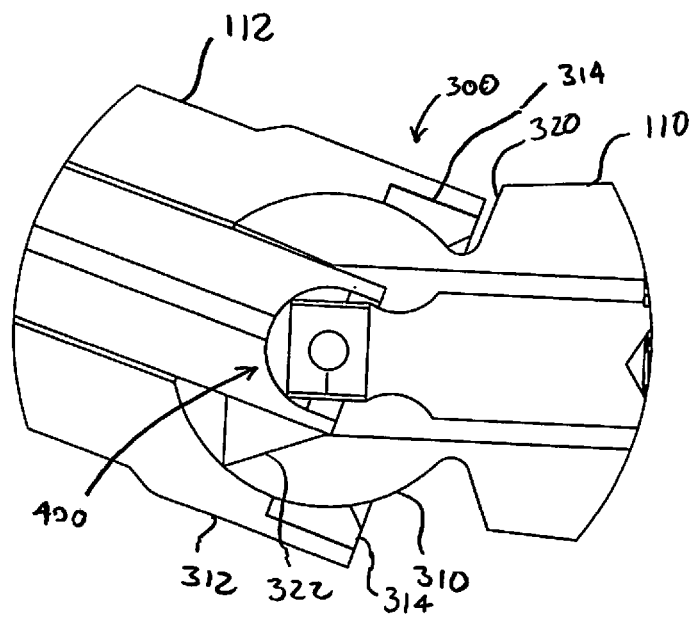
FIG. 5 is a detail, side cross-sectional view of an outer joint of the adjustable angle adapter, in according with the inventive arrangement.

A maximum angle that the body 110 can pivot relative to the nose 112 can be defined by the configuration of the outer joint 300, and any configuration so capable is acceptable for use with the adapter 100. However, in certain aspects, the maximum angle can be defined at a position in which the nose 112 can no longer pivot relative to the body 110. For example, one end of the nose 112 may engage a portion of the body 110 at a particular angle of the nose 112 relative to the body, thereby preventing a further increase in the angle between the body 110 and nose 112. By way of example, referring to FIG. 5 a portion of the nose 112 (e.g., lock 314) will ultimately engage a portion of the body 110 (e.g., shoulder 320). With this configuration, upon the nose 112 engaging the body 110, a maximum angle that the body 110 can pivot relative to the nose 112 can be defined. As will be discussed in greater detail, additional and/or alternative configurations can be used to define the maximum angle that the body 110 can pivot relative to the nose 112.

Figure 13A:
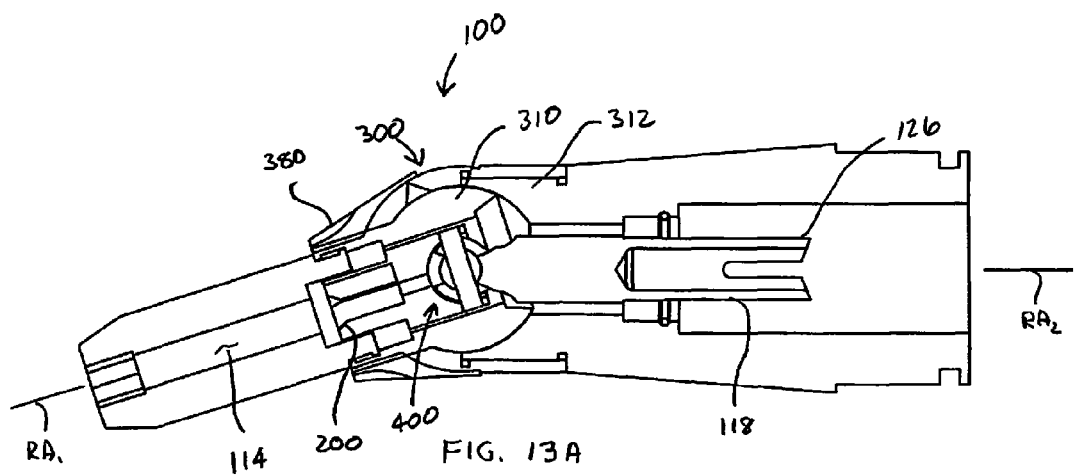
FIGS. 13A and 13B are side cross-sectional views of the adjustable angle adapter, respectively, in contra-style and straight orientations.
Figure 13B:
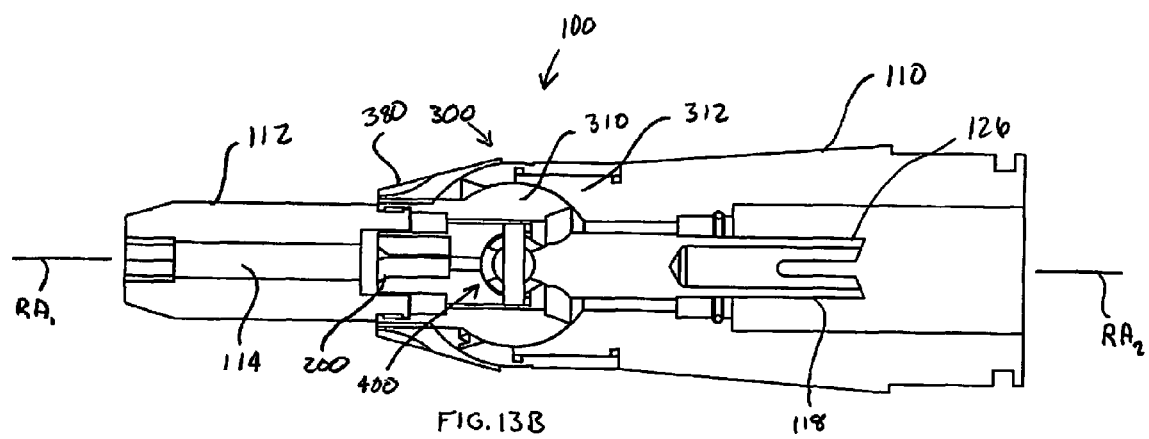

Although the manner by which the outer joint 300 permits the nose 112 to pivot relative to the body 110 is not limited to a certain configuration, in certain aspects of the adapter 100, one of the nose 112 and the body 110 includes a ball-shaped portion 310 and the other of the nose 112 and the body 110 includes a ball receiver 312 configured to receive the ball-shaped portion. For example, referring to FIGS. 13A-13B, the ball receiver 312 may be positioned on the body 110, and the ball portion 310 may be positioned on the nose 112. However, referring to FIGS. 5 and 6A-6B, in one aspect of the outer joint 300, the ball-shaped portion 310 is positioned on the body 110 and the ball receiver 312 is positioned on the nose 112. Additional views of the ball receiver 312 and the ball portion 310 are respectively illustrated in FIGS. 2 and 3.

In operation, the ball receiver 312 surrounds and pivots relative to a section of the ball portion 310. Additionally, the ball receiver 312 may include a removably attachable lock 314 that can be fixed to the ball receiver 312 after the ball portion 310 has been inserted into the ball receiver 312. In so doing, the combination of the ball receiver 312 and the lock 314 can act to prevent the nose 112 from being detached from the body 110. The mating of the ball receiver 312 to the ball portion 310 may be a loose fitting. Alternatively, the ball portion 310 may be a tight fitted to the ball receiver 312.

An additional configuration for defining the maximum angle that the body 110 can pivot relative to the nose 112 is by restricting a maximum angle between the collet 200 and the shaft 118. For example, an inner angled face 322 can similarly act as a physical stop to the rotation of the collet 200 relative to the shaft 118.

However, in certain aspects of the adapter 100, the angle of the angled (or chamfered) face 322 to a centerline of the body 110 is slightly greater than a maximum angle that the body 110 can pivot relative to the nose 112. In so doing, interference between the rotating collet 200 and the non-rotating body 110 can be prevented. Also, by angling the face 322, as opposed to have a face 322 that is perpendicular to the centerline of the collet 200, a greater proportion of the ball portion 310 can be any contact with the inner surface of the ball receiver 312 at any given angular configuration.

Figure 12:
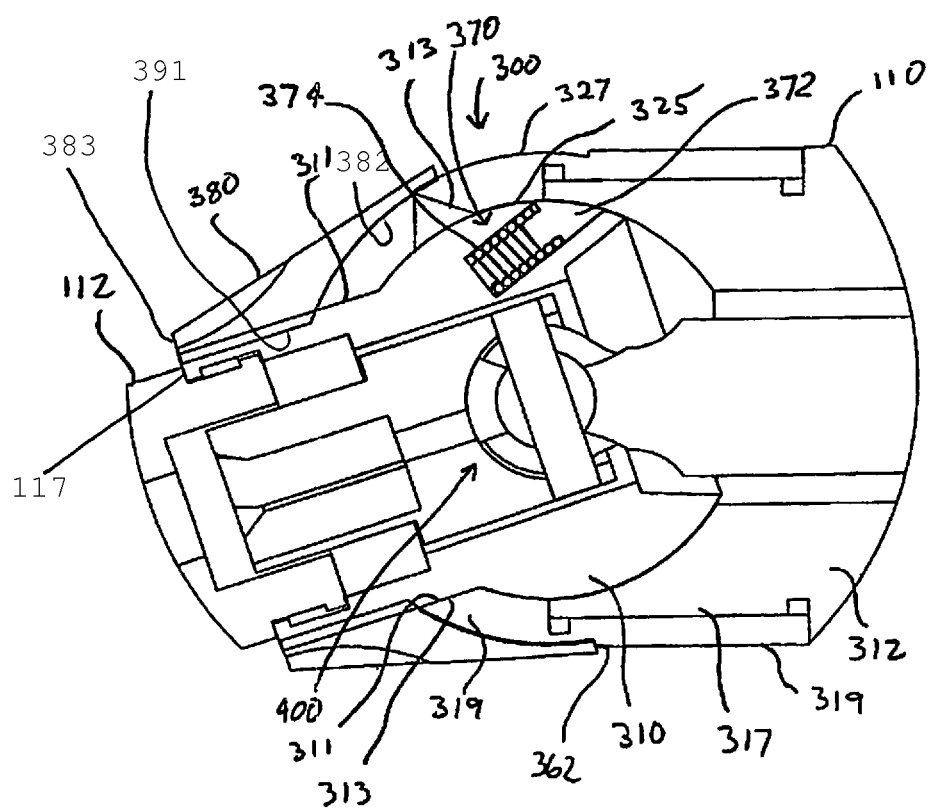
FIG. 12 is a detail, side cross-sectional view of an outer joint of the adjustable angle adapter, in accordance with the inventive arrangement.

Referring to FIGS. 7, 7A, 11A-11B, 12, and 13A-13B, an additional embodiment of the outer joint 300 is illustrated. In this particular embodiment, the ball receiver 312 is positioned on the body 110, and the ball portion 310 is positioned on the nose 112. This embodiment of the outer joint 300 can also includes a stop that defines a maximum angle that the body 110 can pivot relative to the nose 112. Referring specifically to FIG. 12, a portion of the nose 112 (e.g., the neck 311 of ball portion 310) will ultimately engage a portion of the body 110 (e.g., a angled surface 313 of the ball receiver 312 that extends from the inner surface 325 to the outer surface 327 of the ball receiver 312). In this configuration, upon the nose 112 engaging the body 110, a maximum angle that the body 110 can pivot relative to the nose 112 can be defined. Additional and/or alternative configurations can also be used to define the maximum angle that the body 110 can pivot relative to the nose 112.

Figure 7A:
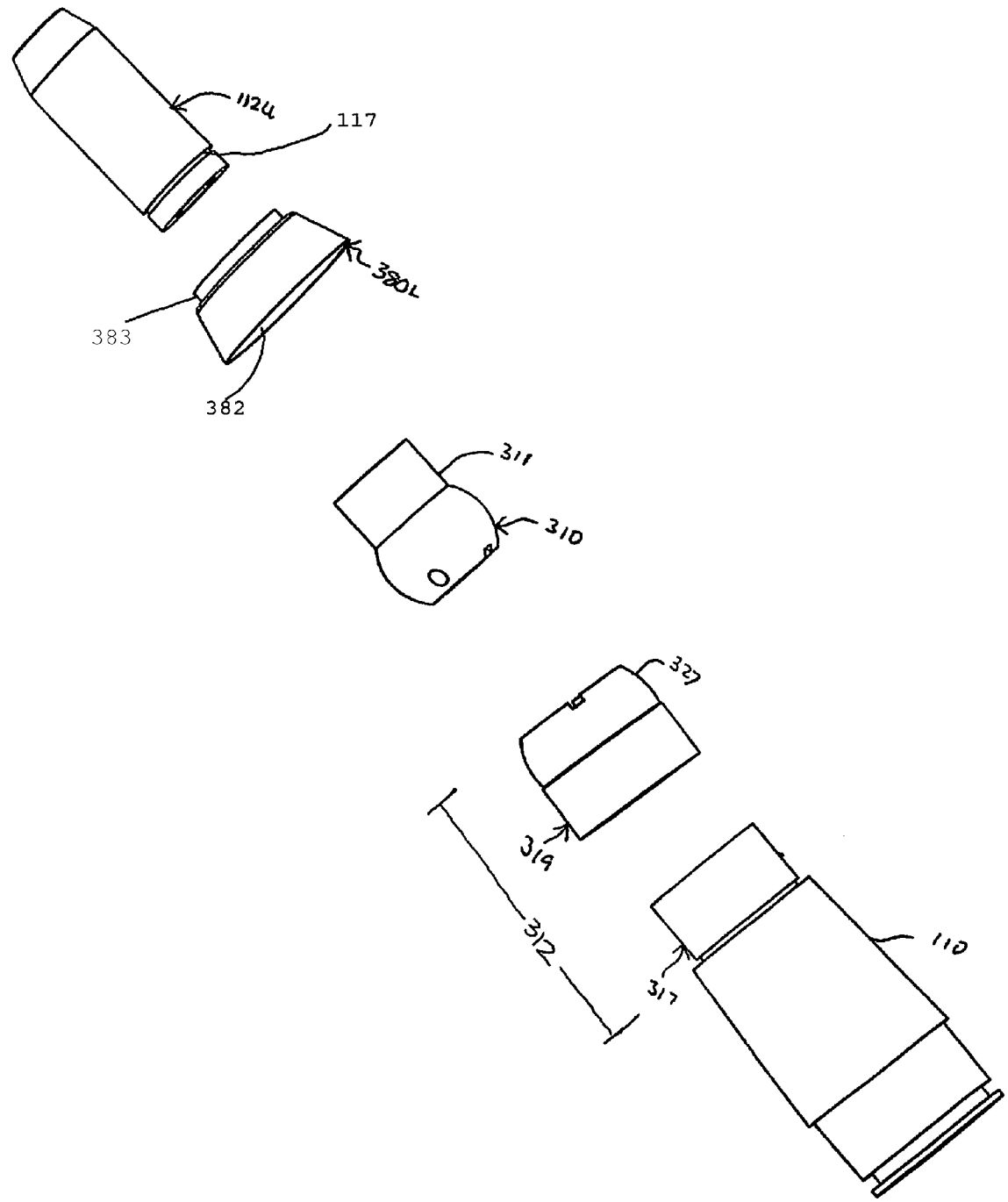
Figure 11A:
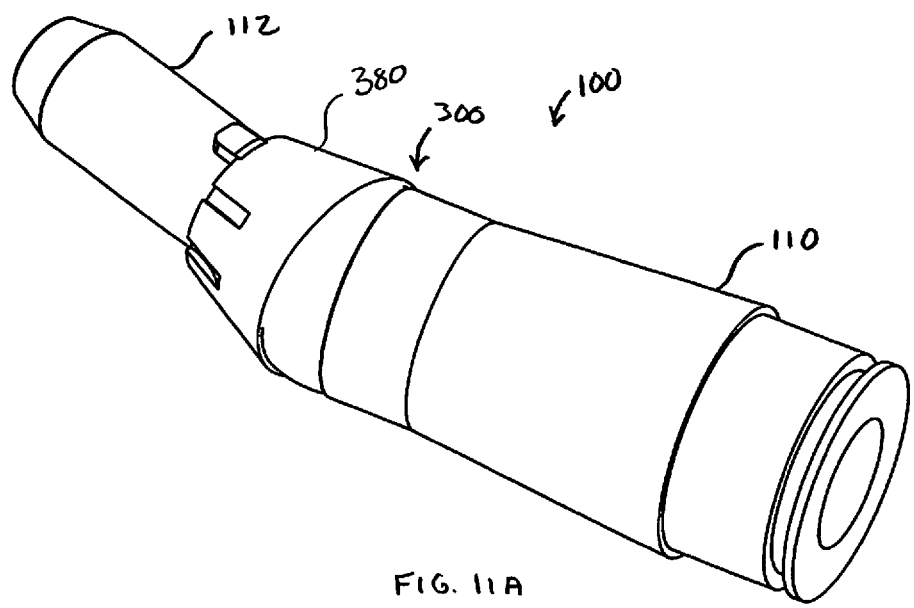
FIGS. 11A and 11B are perspective views of the adjustable angle adapter, respectively, in contra-style and straight orientations.
Figure 11B:
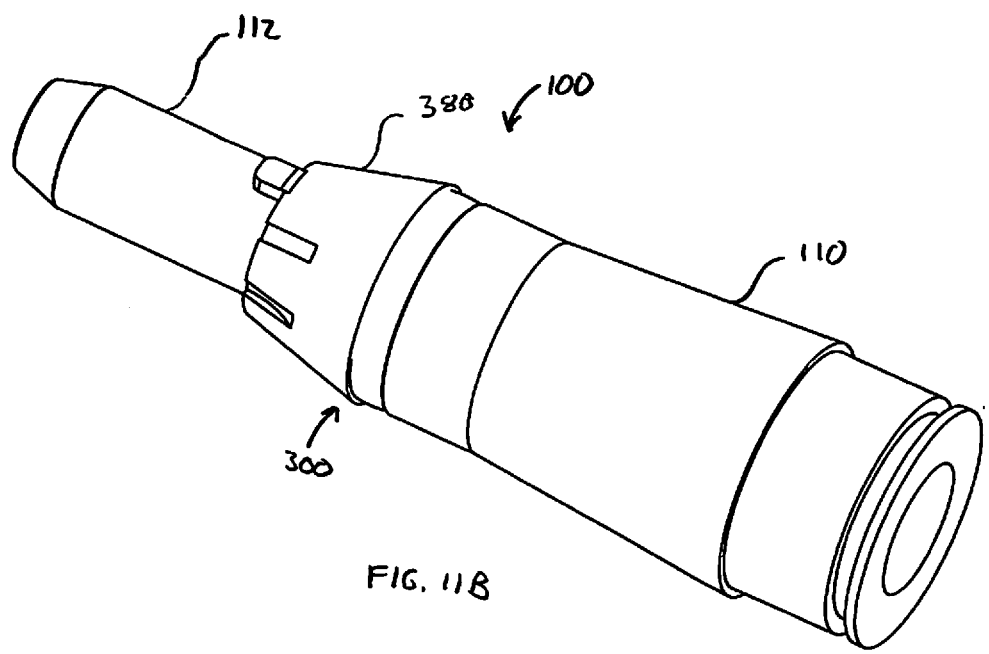

Referring specifically to FIG. 7, the nose 112 and guard 380 can have different configurations relative to one another. For example, in the upper configuration, the nose 112U is inserted fully into the guard 380U and subsequently mates with the neck 311 of the ball portion 310. In the lower configuration, the nose 112L mates with a perpendicular face of the guard 380L. Referring specifically to FIG. 7A, an inner surface 391 (illustrated in FIG. 8A) of one edge 383 of a guard 380L can rest against a lip 117 of a nose 112U and the inner surface 382 of an opposite end of the guard 380L can rest on an outer surface 327 of a second portion 319 of a ball receiver 312. The lip 117 of the nose 112U can be configured to prevent the guard 380L from moving toward the prophy angle. Of note, the inner surface 382 of the guard 380L can be concave. Further, the nose 112U can be configured to pivot relative to the body 110 into at least a first configuration and a second configuration as the guard 380L moves along the outer surface 327 of the second portion 319 of the ball receiver 312. As can be readily envisaged, other configurations are possible.

Additionally, by angling the surface 313, as opposed to have a face that is perpendicular to the inner surface 325 or the outer surface 327 of the ball receiver 312, a greater proportion of outer surface 327 of the ball receiver 312 can be any contact with an inner surface 382 of a guard 380 at any given angular configuration.

Referring specifically to FIG. 12, In certain aspects of the adapter 100, one or more drag devices 370 may be included within the outer joint 300, the drag devices 370 act to increase the drag between the ball portion 310 and ball receiver 312 as the nose 112 pivots relative to the body 110. By increasing the drag between the ball portion 310 and the ball receiver 312, the nose 112 is less likely to pivot relative to the body 110 during use of the adapter 100 and after the adjustment of the angle between the body 110 and the nose 112. Additionally, although the drag device 370 is illustrated with respect to the additional embodiment, the adapter 100 is not limited in this manner, and the drag device 370 can be employed in the previous embodiment.

Although a single drag device 370 is illustrated, more than a single drag device 370 can be employed. Also, if more than a single drag device 370 is employed, these drag devices can be positioned equidistant to one another. In certain aspects of the outer joint 300, three drag devices 370 are provided and positioned 120 degrees apart.

Any type of drag device 370 capable of increasing the drag between the ball portion 310 and the ball receiver 312 as the nose 112 pivots relative to the body 110 is acceptable for use in the joint 300. However, in certain aspects, the drag device 370 includes a plunger 372 and a biasing means (e.g., a spring 374) positioned within a channel of either the ball receiver 312 or the ball portion 310. As illustrated, the drag device 370 is positioned within the ball portion 310. In certain aspects of the drag device 370, the outer surface of the plunger 372 substantially matches the outer radius of the ball portion 310.

Although not limited in this manner, the assembly of the additional embodiment of adapter 100 involves splitting the ball receiver 312 into two separate portions 317, 319. The first portion 317 is connected to the body 110 and the second portion 319 is attachable to the first portion 317 using, for example, mating threads. While the second portion 319 of the ball receiver 312 is separate from the first portion 317 of the ball receiver 312, the ball portion 310 is inserted into the cavity defined by the inner surface 325 of the ball receiver 312. The second portion 319 of the ball receiver 312 is then slid over the ball portion 310 and attached to the first portion of the ball receiver 312. In so doing, the body 110 is joined to the nose 112 at the outer joint 300.

Referring again to FIGS. 8A-8B, 12 and 13A-13B, a guard 380 can be provided that creates a seal between the nose 112 and the ball receiver 312. The guard 380 includes an inner surface 382 having a radius that substantially matches a radius of the outer surface 327 of the ball receiver 312. The guard 380 can also include an additional inner surface 391 that is predominantly flat. Additionally, the guard 380 can include a sealing element 386 that engages the outer surface 327 of the ball receiver 312 to form a seal. This seal acts to prevent debris, during operation of the adapter 100, from entering the outer joint 300. As the nose 112 pivots relative to the body 110, the sealing element 386 remains substantially in contact with the outer surface 327 of the ball receiver 312 to maintain the seal between the nose 112 and the ball receiver 312. Further, as seen in FIG. 12, an inner surface 391 of one end of the guard 380 can rest on a neck 311 of a ball portion 310 and the inner surface 382 of an opposite end of the guard 380 can rest on an outer surface 327 of a second portion 319 of the ball receiver 312. More specifically, as an edge 383 of the guard 380 can rest against the lip 117 of the nose 112. In addition, the guard 380 can move along the outer surface 327 of the second portion 319 of the ball receiver 312 as the nose 112 pivots relative to the body 110 into at least a first configuration and a second configuration.

Although not limited in this manner, the engagement of the guard 380 and the ball receiver 312 can act to define a maximum angle that the body 110 can pivot relative to the nose 112. For example, referring specifically to FIG. 12, at a particular angle of the body 110 relative to the nose 112, the distal end of the guard 380 may engage a shoulder 362 in the outer surface 327 of the ball receiver 312. In this manner, the maximum angle that the body 110 can pivot relative to the nose 112 can be defined.

Referring to FIG. 8A, the inner surface 382 of the guard 380 may include a plurality of inwardly-extending ribs 384 to engage the outer surface 327 of the ball receiver 312. The ribs 384 provide a grabbing surface with which the guard 380 can prevent movement of the guard 380 relative to the ball receiver 312 upon outside pressure being placed against the guard 380, thereby preventing movement of the body 110 relative to the nose 112. Although the ribs 384 are illustrated as being disposed on the guard 380, the ribs 384 may be disposed on the outer surface 327 of the ball receiver 327 Additionally, although the ribs 384 are illustrated as radiating from a center, the ribs 384 may be configured to constitute a plurality of concentric circles.

By their very nature, seals tend to wear over time and/or use and become less effective. In certain aspects of the outer joint 300, the guard 380 can be considered a replaceable portion of the adapter 100. Also, although not limited in this manner, the guard 380 can be formed from an easily-fashioned material, such as autoclavable plastic. The outer joint 300 is not limited in the manner in which the guard 380 can be replaceable. For example, referring to FIGS. 7 and 7A, the guard 380U, 380L may be removably attachable to the nose 112U, 112L, and the manner by which the guard 380U, 380L is removably attachable to the nose 112U, 112L is not limited. For example, the guard 380U, 380L may screw onto the nose 112U, 112L. Alternatively, one or more removable pins may be used to attach the guard 380U, 380L to the nose 112U, 112L. Additionally, the guard 380U may screw onto the neck 311 of the ball portion 310. In certain aspects, the guard 380L floats between the nose 112L and the ball receiver 327.

Figure 14A:
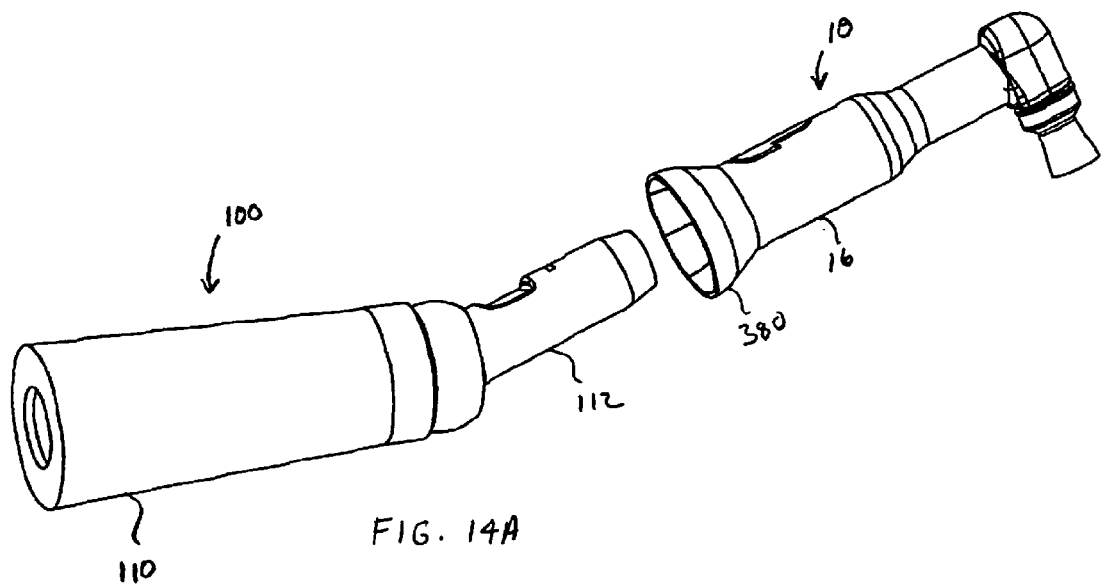
FIGS. 14A and 14B are perspective views of a prophy angle with an integrated guard detached and attached to an adjustable angle adapter, in accordance with the inventive arrangements.
Figure 14B:
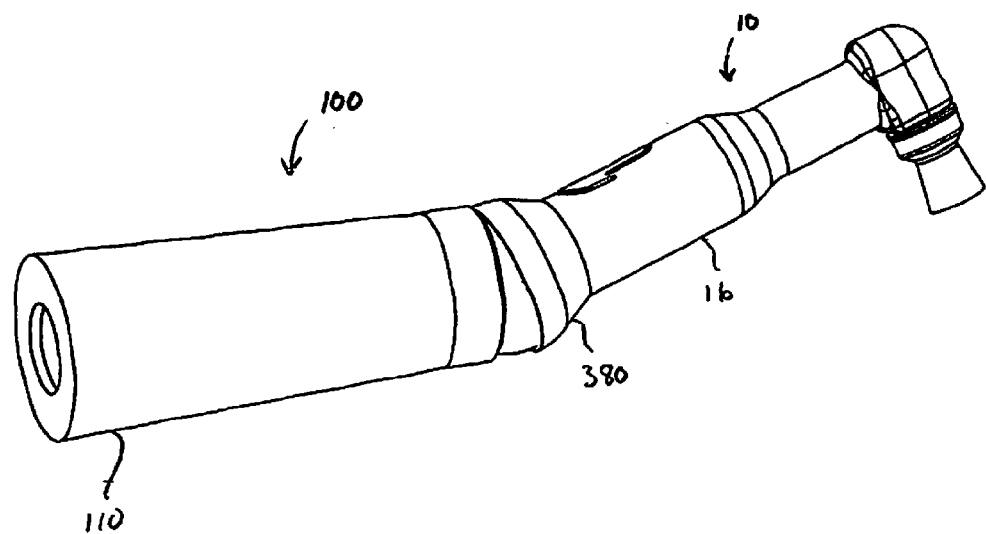
Figure 15:
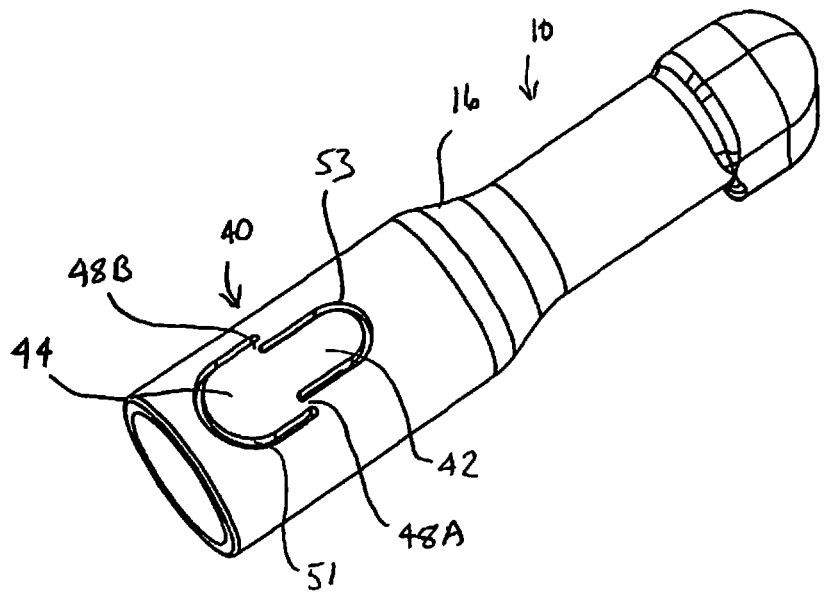
FIG. 15 is a perspective view of a prophy angle with latching mechanism, in accordance with the inventive arrangements.
Figure 16:
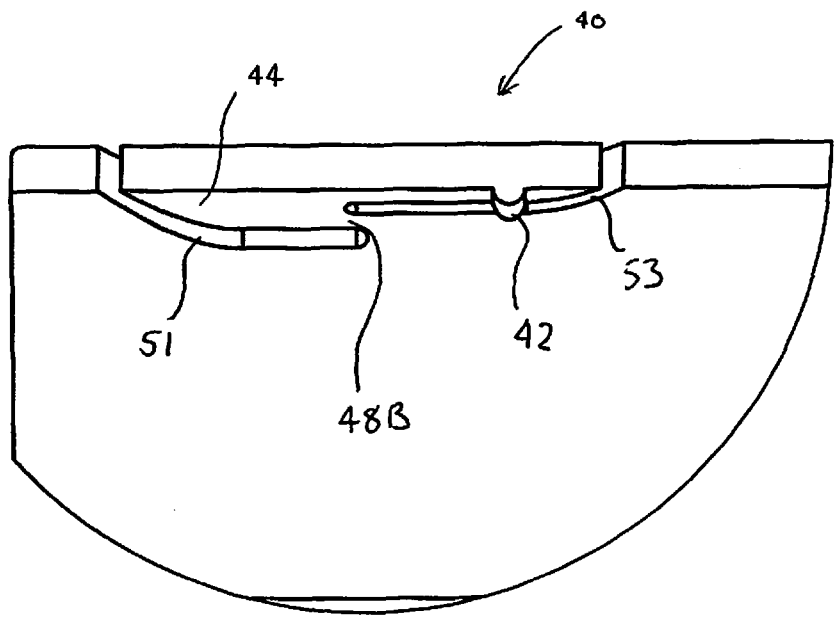
FIG. 16 is a side cross-sectional view of the latching mechanism.
Figure 17A:
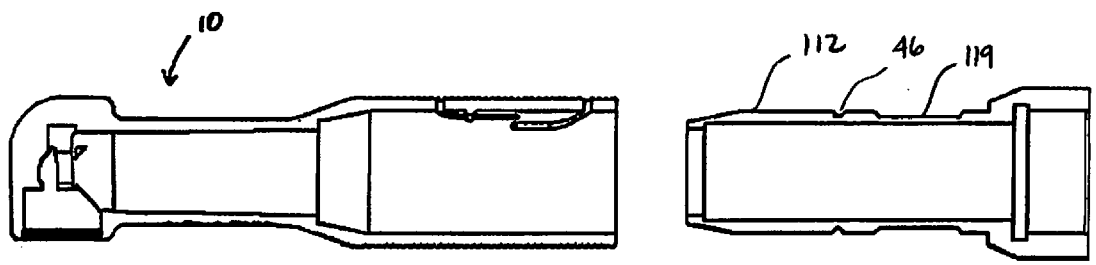
FIGS. 17A-17D are, respectively, cross-sectional view of the prophy angle with latching mechanism and nose of the adapter in a disassembled, partially-assembled, fully-assembled and latched, and full-assembled and unlatched configurations.
Figure 17B:
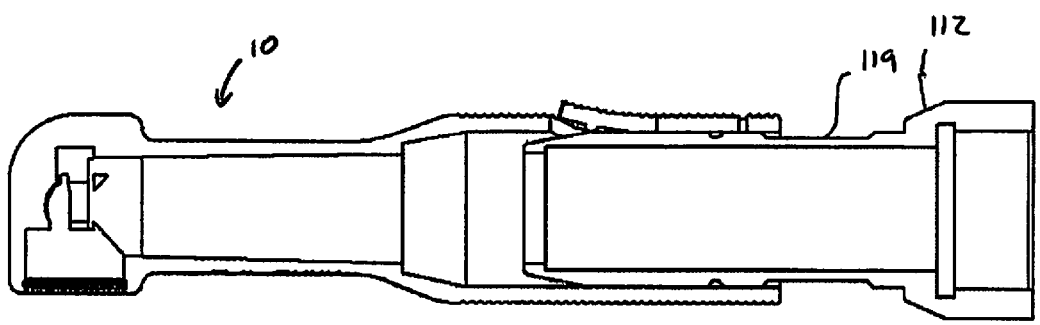
Figure 17C:
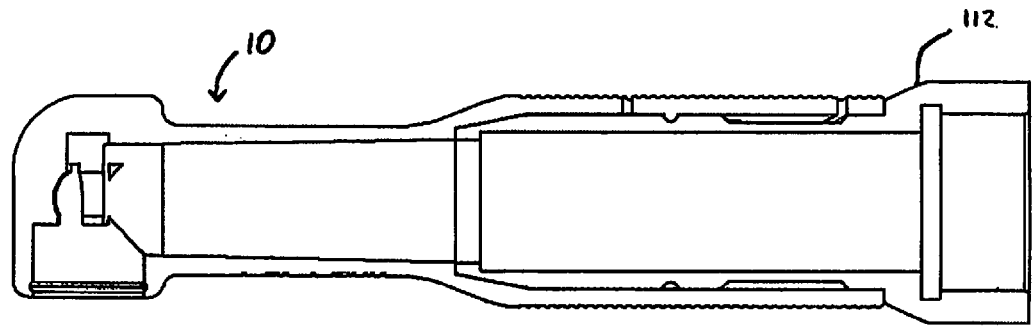
Figure 17D:
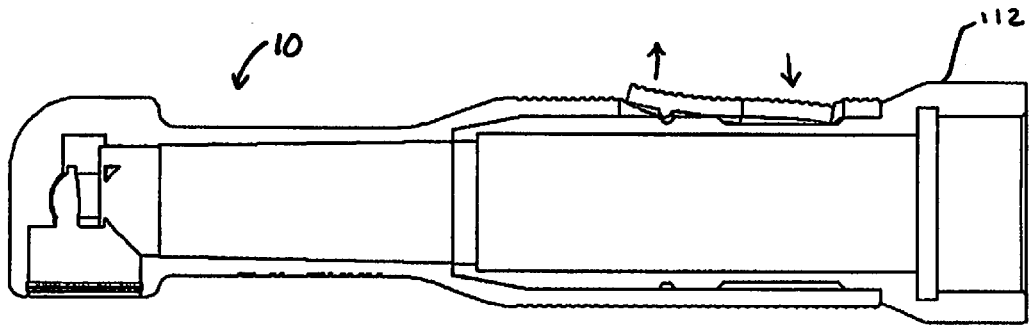

Referring to FIG. 14, the guard 380 may be integrated into the housing 16 of the prophy angle 10. Since common practice is to treat the prophy angle 10 as a disposable item that is replaced each time the adapter 100 is used with a new patient, the guard 380 can also be replaced each time the prophy angle 10 is replaced. Since the guard 380 acts as a seal between the nose 112 and the ball receiver 312, each instance the prophy angle 10 is replaced, a new seal is provided between the nose 112 and the ball receiver 312.

As illustrated, the guard 380 extends from a receiving end of the housing 16. Additionally, the guard 380 has a greatest outer diameter is larger than a greatest outer diameter of the housing 16. In certain aspects, the greatest outer diameter of the guard 380 is 10% greater than the greatest outer diameter larger than a greatest outer diameter of the housing 16. In other aspects, the greatest outer diameter of the guard 380 is 20% greater than the greatest outer diameter larger than a greatest outer diameter of the housing 16.

With a prophy angle 10 having a prophy rotating member 12 (i.e., a shaft), engagement of the prophy rotating member 12 and the collet 200 of the adapter 100 functions to prevent removal of the prophy angle 10 from the nose 112. The prophy rotating member 12 is typically inserted into the collet 200, which holds the prophy rotating member 12 in place and prevents removal of the prophy rotating member 12 from collet 200. However, with shaft-less prophy angles, the shaft is an integral part of the nose 112. Thus, since connection is not present in a shaft-less prophy angle, there is a need for a latching mechanism that prevents removal of the prophy angle from the nose 112. An example of a shaft-less prophy angle is described in U.S. patent application Ser. No. 11/862,628, filed on Sep. 27, 2007, which is incorporated herein by reference in its entirety.

Referring to FIGS. 24A and 24B, a shaft-less prophy angle 10SL and an adapter 10 with an integrated drive shaft 350 is illustrated. Although illustrated with a non-adjustable adapter 10, these concepts are also applicable to an adjustable adapter 10 such as that illustrated in FIGS. 1 and 7. The adapter 10, directly or indirectly, provides the rotational movement to a gearing system of a rotor 20 of the prophy angle 10SL. The adaptor 100 includes a body 110 and a nose 112. The adapter 100 includes a shaft 118 that is connected to a drive shaft 350 via a coupler 400.

The shaft 118 is rotated by the drive source 450. As is known in the art, many different types of drive sources 450 exist and these different drive sources 450 have different configurations for coupling with a rotating member, such as the shaft 118. In this regard, the present adapter 100 is not limited as to drive source 450 for the adapter 100. For example, the drive source 450 may be connectable to the adapter 100. Alternatively, the drive source 450 may be integrated with the adapter 100. Also, examples of drive sources 450 include electrically-driven and pneumatically-driven motors.

As illustrated, the drive shaft 350 is a part of the adaptor 100. In other aspects, the drive shaft 350 is removably attachable to a collet within the adaptor 100. In so doing, the drive shaft 350 can be replaceable and/or cleaned. A slideable sleeve 460 may be positioned over the drive shaft 350. The slideable sleeve 460 moves from an extended position (FIG. 24A), which conceals the gear 352 of the drive shaft 350, to an retracted position (FIG. 24B), which reveals the gear 352 of the drive shaft 350. The slideable sleeve 460 is not limited in the manner in which the slideable sleeve 460 moves from the extended position to the retracted position and back again. The gear 352 is configured to engage the prophy angle 10 to drive rotor 20.

Referring to FIGS. 15-16 and 17A-17D, a prophy angle 10 with a latching mechanism 40 is illustrated. The latching mechanism 40 includes a male/female latch element 42 and a lever 44 that engages and/or disengages the male/female latch element 42. The nose 112 of the adapter 100 also includes a female/male element 46 that is configured to engage the male/ female element 42 of the latching mechanism 40 in the prophy angle 10. Although the latching mechanism 40 is illustrated with a shaft-less prophy angle 10, the latching mechanism 40 may also be employed with a prophy angle having a prophy rotating member 12 (i.e., shaft).

Although FIGS. 15 and 17A-17D illustrate the latch element 42 as a male element and element 46 of the nose 112 as a female element, these configurations can be swapped. In operation, referring to FIG. 17B, as the prophy angle 10 is placed over the nose 112, the nose 112 displaces the latch element 42 from its resting orientation relative to the remainder of the prophy angle 10. However, referring to FIG. 17C, as the prophy angle 10 is fully inserted onto the nose 112, the latch element 42 is released from its displaced orientation and is positioned within the female element 46 (e.g., a groove) in the nose 112. In so doing, the latch element 42 prevents removal of the prophy rotating member 12 from collet 200.

Referring to 17D, to release the latching mechanism 40, the lever 44 is depressed (see down arrow), which acts to rotate the latch element 42 about a pair of pivots 48A, 48B and out of the groove 46 in the nose 112 (see up arrow). To permit depressing of the lever 44, a depression 119 is formed in the outer surface of the nose 112 proximate the groove 46. Thus, as illustrated, movement of the lever 44 between a first position (e.g., FIG. 17C) and a second position (e.g., 17C) moves the latch element 42 between an engaged position and a disengaged position.

Referring again to FIG. 15, although not limited to this particular configuration, each one of the pair of pivots 48A, 48B is defined by a pair of substantially parallel and overlapping slots 51, 53 within the housing. Also, a first one 51 of the pair of slots of the first pivot 48A connects to a first one 51 of the pair of slots of the second pivot 48B, and a second one 53 of the pair of slots of the first pivot 48A connects to a second one 53 of the pair of slots of the second pivot 48B. The latch mechanism 40 may be formed from the housing 16 of the prophy angle 16. Although not limited to this particular configuration, the lever action of the latch mechanism 40 may be formed by including a pair of opposing U-shaped slots 51, 53 within the housing 16. Additionally, the latch element 42 may be disposed within the bounds of the U-Shaped slot 42 within the housing 16. As can be readily envisaged, the slots 51, 53 are not limited to a U-shape. For example, one or both of the slots 51, 53 could be V-shaped, rectangular-shaped, or shaped like a half moon.

Referring to FIGS. 1, 6A-6B, 7, and 13A, 13B, the outer portion of the nose 112 may be shaped to mate with the prophy angle 10. As is known in the art, many types of different types of prophy angles 10 exist that have different mating profiles, and the present adapter 100 is not limited as to a particular shape of the nose 112 and as to a particular profile of prophy angle 10 with which the nose 112 can mate. However, in a certain aspects of the adapter 100, the nose 112 is a configured as a doriot-style adapter. Depending upon the type of prophy angle 10, other type of connections devices include, but are not limited to, latch type, 3-ball chuck, attachment ring, push chuck, quick-connect collars, autochucks, E-type (i.e., ISO 3964), DIN 13940, ISO 1797, U-type, NSK type, and Midwest type.

The body 110 includes a second bore 116 for receiving the shaft 118 and, in certain configurations, also a portion of the prophy rotating member 12. Additionally, the inner surface of the second bore 116 of the body 110 may be shaped to mate with a drive source, such as a micromotor. As is known in the art, many different configuration of drive sources exist that have different mating profiles, and the present adapter 100 is not limited as to a particular profile of the second bore 116 with which the drive source can mate.

As is known in the art, many different types of drive sources exist and these different drive sources have different configurations for coupling with a rotating member, such as the shaft 118. In this regard, the present adapter 100 is not limited as to the type and configuration of coupler 126 that couples with the drive source. However, in certain aspects of the adapter 100, the coupler 126 is an E-type coupler. Other types of couplers/connection devices have been previously described with regard to the nose 112.

The shaft 118 is rotated by the drive source, which is connected to a coupler 126 positioned on one end of the shaft 118, which drives a collet 200 connected on another end of the shaft 118. In certain configurations of the adjustable angle adapter 100, both the coupler 126 and the collet 200 rotate about a common rotational axis RA. However, as previously discussed, in other configurations of the adjustable angle adapter 100, the coupler 126 and the collet 200 rotate about different rotational axes $RA_1$, $RA_2$.

Many types of shafts 118 are capable of transmitting rotation from the coupler 126 to the collet 200, and the present adjustable angle adapter 100 is not limited as to a particular type of shaft 118 so capable. As the rotational axis $RA_2$ of the shaft 118 may be at an angle to the rotational axis $RA_1$ of the collet 200, a multi-axis rotation joint 400 (see discussion with regard to FIGS. 19A-19C and 20A-20B) is positioned between the collet 200 and the shaft 118 to transfer the rotation of the shaft 118 to the collet 200.

Figure 18A:
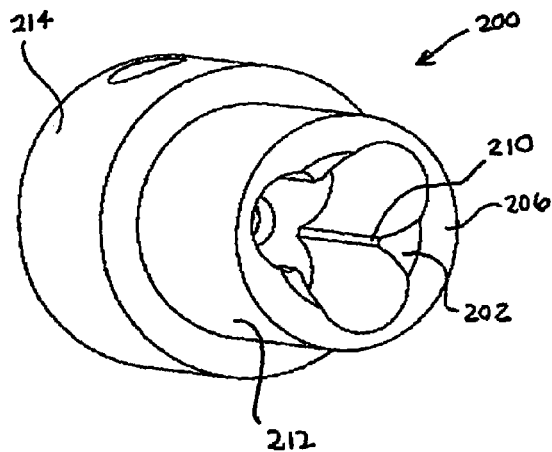
FIGS. 18A-18C are, respectively, a front perspective view, a front plan view, and a side cross-sectional view of a collet in accordance with the inventive arrangements.
Figure 18B:
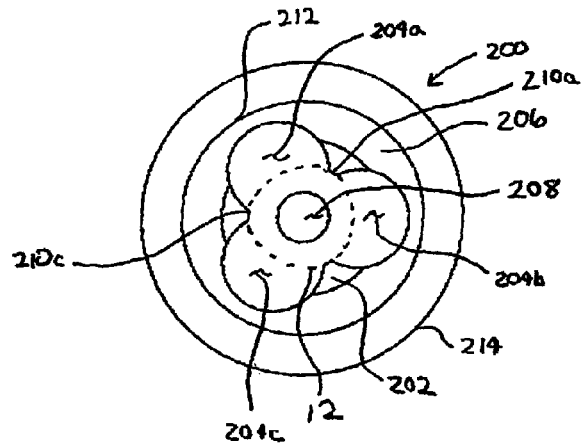
Figure 18C:
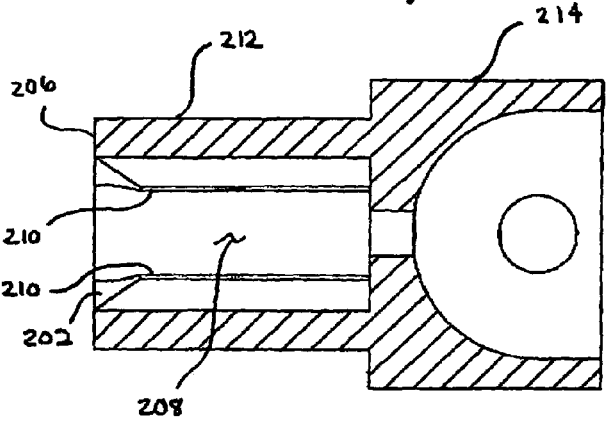

FIGS. 18A-18C further illustrate the collet 200. The collet 200 of the adapter 100 is adapted to receive and hold the prophy rotating member 12 of the prophy angle 10. In certain aspects of the adapter 100, the collet 200 is not limited in the manner in which the collet 200 receives and holds the prophy rotating member 12, and any configuration of the collet 200 so capable is acceptable for use with the adapter 100.

In certain aspects of the adapter 100, the collet 200 includes a plurality of extensions 210a-210c for receiving the prophy rotating member 12. The innermost portions of the extensions 210a-210c define an inner collet bore 208 having a diameter slightly less than the diameter of the prophy rotating member 12. In this manner, upon the prophy rotating member 12 being positioned within the inner collet bore 208, an interference fit or friction grip exists between the plurality of extensions 210a-210c and the prophy rotating member 12. The interference fit allows the extensions 210a-210c to hold onto the prophy rotating member 12 and to transfer rotation from the collet 200 to the prophy rotating member 12. In certain aspects of the collet 200, the innermost portions of the extensions 210a-210c define an inner collet bore 208 having a fixed diameter.

As illustrated in FIG. 18A, the outer edge of each extension 210a-210c may also include a concave surface. The concave surfaces of the extensions 210a-210c can define the outer circumference of the inner collet bore 208 of the collet 200. These concave surfaces also mate with the outer surface of the prophy rotating member 12 to form the interference fit between the plurality of extensions 210a-210c and the prophy rotating member 12. Although not limited in this manner, the radius of the concave surfaces of the extensions 210a-210c is substantially equal to the radius of the collet bore 208. Although not limited in this manner, in certain aspects of the collet 200, the concave surfaces define less than 20% of the circumference of the collet bore 208.

The collet 200 may also include longitudinal chamfers 202 on the extensions 210a-210c. The chamfers may extend from a collet distal end 206 along each extension 210a-210c and slope inwardly towards the rotational axis of the collet 200. The longitudinal chamfers 202 provide a guide for receiving the prophy rotating member 12. As the prophy rotating member 12 is moved into the collet 200, the longitudinal chamfers 202 guide the prophy rotating member 12 toward the inner collet bore 208. Although not limited in this manner, a face of the longitudinal chamfers 202 may be angled at about 60°±15° relative to the face of the distal end 206 of the collet 200.

The manner in which the inner collet bore 208 is formed is not limited. For example, the inner collet bore 208 may be formed by drilling the collet 200 along its centerline. By forming the inner collet bore 208 is this manner, the concave surfaces at the outer edge of each extension 210a-210c may also be formed. Also, the extensions 210a-210c may be formed by drilling offset bores 204a-204c, which have a centerline offset from the centerline of the collet 200. Although the term "drilling" is used herein, other methodology used to form bores/holes is also acceptable.

Many types of joints are capable of transferring rotation from a first rotating member to a second rotating member, which is positioned off-axis from the first rotating member, and the present adjustable angle adapter 100 is not limited as to a particular type of joint so capable. In a current aspect of the adapter 100, the multi-axis rotation joint 400 is a yoke and joint, as illustrated in 19A-19C and 20A-20B.

Figure 19A:
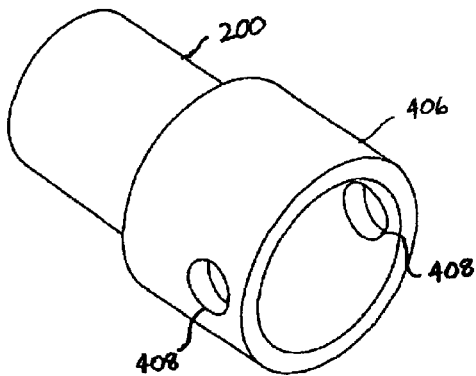
FIGS. 19A-19D are, respectively, a perspective view of a receiver, a perspective view of the receiver and a second pin, a perspective view of a first pin and the second pin, and a perspective view of the first pin and the second pin position within a head of a yoke and pin joint in accordance with the inventive arrangements.

Referring to FIGS. 19A-19C and 20A, 20B, elements of a multi-axis rotation joint 400 are illustrated. Referring to FIG. 19A, the collet 200 is connected to a receiver 406 for receiving a head 410 of the multi-axis rotation joint 400. Although shown connected to the collet 200, the receiver 406 may be integral with the collet 200. Alternatively, another member (not shown) may be positioned between the receiver 406 and the collet 200. The use of a multi-axis rotation joint 400 advantageously reduces back lash, which is inherent in many types of joints.

Figure 19B:
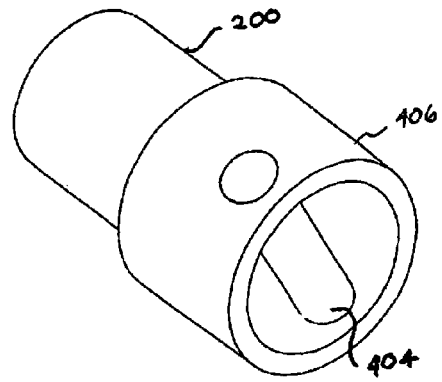

Referring to FIGS. 19A and 19B, the receiver 406 includes openings 408 into which a second pin 404 is positioned. Although the second pin 404 may rotate within the openings 408 of the receiver 406, in a current aspect of the multi-axis rotation joint 400, the second pin 404 is positionally and rotationally fixed relative to the receiver 406. In so doing, the second pin 404 is prevented from moving within the receiver 406. Since the receiver 406, and thus the ends of the second pin 404, can rotate about the rotational axis $RA_1$ of the collet 200 at very high speeds, any movement of the ends of the second pin 404 beyond the outer circumference of the receiver 406 may cause engagement between the ends of the second pin 404 and inner surfaces of the nose 312 and/or the body 110 of the adapter 100. This engagement may cause failure of or damage to the adapter 100 and/or the multi-axis rotation joint 400.

The manner in which the second pin 404 is prevented from moving within the receiver 406 is not limited as to a particular technique or arrangement. For example, the second pin 404 can be attached to the receiver, for example, via welding or gluing. However, in a current aspect of the multi-axis rotation joint 400, the second pin 404 is sized slightly greater than the size of the openings 408 of the receiver 406 such that upon inserting the second pin 404 into openings 408, an interference fit exists between the second pin 404 and the openings 408.

Figure 19C:
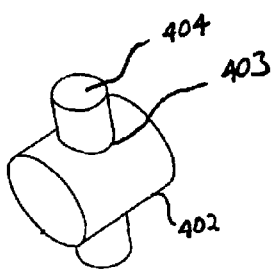
Figure 19D:
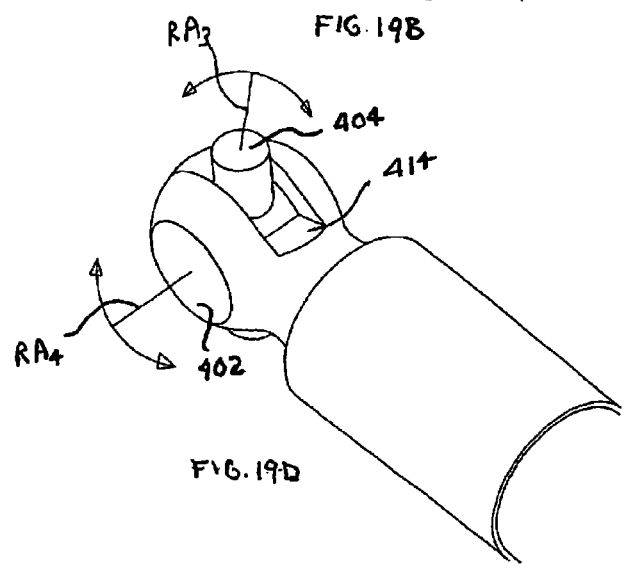
Figure 20A:
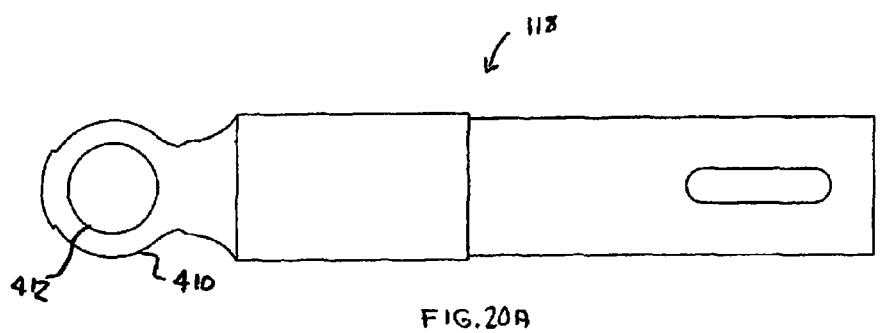
FIGS. 20A and 20B are, respectively, side and top views of the head of the multi-axis rotation joint and a shaft to which the head is connected.
Figure 20B:
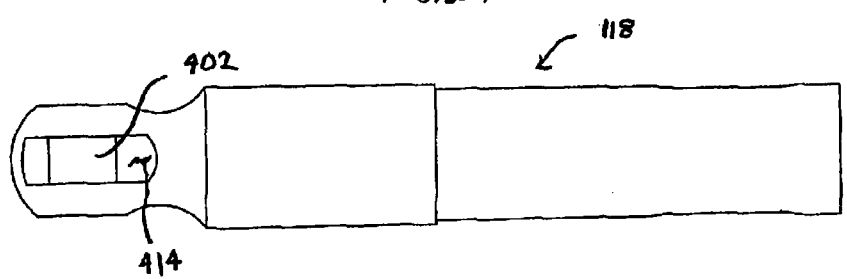

Referring to FIGS. 19C and 19D, the second pin 404 is positioned within an opening 403 of a first pin 402, and the first pin 402 is positioned within a head 410. As also illustrated in FIGS. 20A and 20B, the head 410 includes slots 414 through which the second pin 404 extends. As presently configured, the first pin 402 rotates within and relative to the head bore 412 of the head 410 about a rotational axis $RA_4$, and the second pin 404 rotates within relative to the first pin 402 about a rotational axis $RA_3$. The outside diameter of the second pin 404 is somewhat less than the inside diameter of the inside diameter of the opening 403 of the first pin 402 to form a close tolerance slip fit between the second pin 404 and the first pin 402. Similar, the outside diameter of the first pin 402 is somewhat less than the inside diameter of the head bore 412 of the head 410 to form a close tolerance slip fit between the first pin 402 and the head bore 412 of the head 410.

Although not limited as to a particular range of rotation or to the particular manner described herein, the first pin 402, while within the head 402, is limited in its range of rotation by the length of the slot 414 in the head 410. As the length of the slot 414 increases, the range of the rotation of the first pin 402 within the head 410 is also increased. Conversely, upon the length of the slot 414 decreasing, the range of rotation of the first pin 402 within the head 410 is also decreased. The width of the slots 414 may be slightly less than the outside diameter of the second pin 404 to allow the second pin 404 to move from side-to-side within the slots 414.

With regard to the range of rotation of the second pin 404 within the first pin 402, the range of rotation is not necessarily limited when the first pin 402 is within the second pin 404 alone. However, upon the joint 400 being fully assembled, the range or ration of the second pin 404 within the first pin 402 may be limited to some degree by interference between the collet 200 and the shaft 118.

Although illustrated as the head 410 being connected to the shaft 118 and the receiver 406 being connected to the collet 200, the multi-axis rotation joint 400 is not limited in this manner. For example, the head 410 may be connected to the collet 200, and the receiver 406 may be connected to the shaft 118.

Unlike many other types of joints, a multi-axis rotation joint 400 allows for the angle between the rotational axis $RA_2$ of the shaft 118 and the rotational axis $RA_1$ of the collet 200 to be varied. Thus, use of the multi-axis rotation joint 400 permits the adjustable angle adapter 100 to be adjusted while the shaft 118 and collet 200 are rotating. To further enable the adjustable angle adapter 100 to be adjusted during the rotation of the shaft 118 and collet 200, the nose 112 pivots relative to the body 100 about a point that is congruent with the intersection point between the rotational axes $RA_1$, $RA_2$ of the collet 200 and shaft 118.

Figure 21:
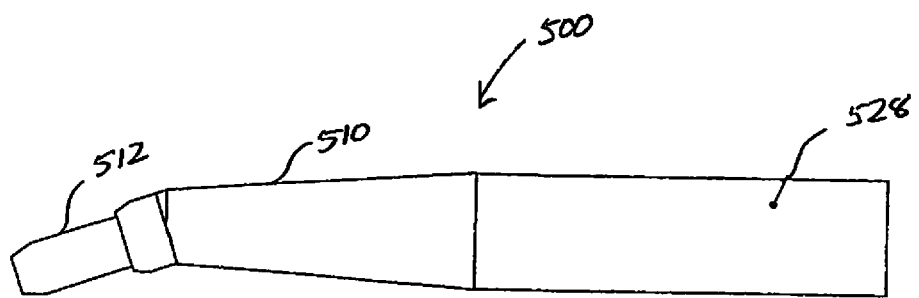
FIG. 21 is a side view of an adapter with an integral micromotor.
Figure 22:
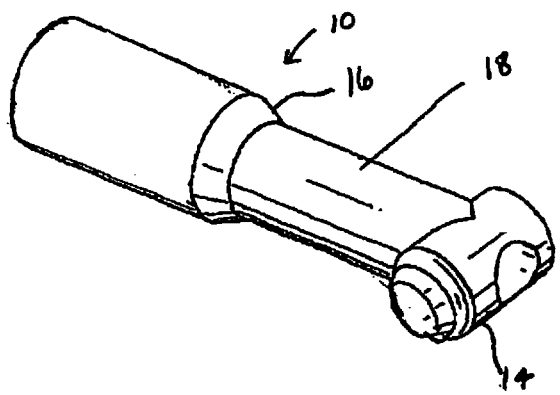
FIG. 22 is a perspective view of a prophy angle according to the prior art.
Figure 23:
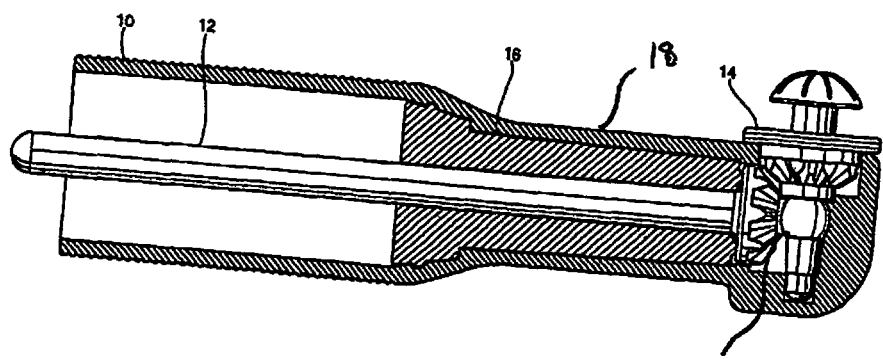
FIG. 23 is a side cross-sectional view of the prophy angle according to the prior art.

FIG. 21 illustrates an adjustable angle adapter 500 with an micromotor 528 that is integral with the body 510 of the adjustable angle adapter 500. Upon using an integral micromotor 528 with the adjustable angle adapter 500, the shaft 518 may be directly connected to both the micromotor 528 and joint 400. Using micromotors to drive dental equipment is well known by those in the art, and any micromotor 528 so capable is acceptable for use with the adjustable angle adapter 500. Examples of micromotors 528 include electrically-driven and pneumatically-driven motors. In the presently-illustrated adjustable angle adapter 500, the micromotor 528 is pneumatically driven.

What is claimed is:

1. An adjustable angle adapter for a prophy angle, comprising:
   a nose configured to receive a portion of a prophy angle;
   a body having two ends, a first end adjustably connected to the nose and a second end opposite the first end, coupled to a power source;
   an outer joint including:
   a ball portion positioned on the nose, a ball receiver positioned on the body, the ball receiver comprising a first portion and a second portion, the first portion coupled to the first end of the body, the second portion attachable to the first portion; and, a guard with an edge of one end of the guard resting against a lip of the nose and an inner surface of an opposite end of the guard resting on an outer surface of the second portion of the ball receiver, the inner surface of the guard being concave, the lip of the nose configured to prevent the guard from moving toward the prophy angle, wherein the nose is configured to pivot relative to the body into at least a first configuration and a second configuration as the guard moves along the outer surface of the second portion of the ball receiver.

2. The adjustable angle adapter of claim 1, wherein
in the first configuration, the nose and the body share a common centerline; and
in the second configuration, a centerline of the body is at a non-zero degree angle to a centerline of the nose.

3. The adjustable angle adapter of claim 1, further comprising
a rotating member disposed within the nose,
a shaft disposed within the body, and
a multi-axis rotation joint connecting the shaft to the rotating member, wherein
the multi-axis rotation joint and the outer joint pivot about a common pivot point.

4. The adjustable angle adapter of claim 1, wherein
the nose is configured to pivot relative to the body from between zero degrees to about eighteen degrees.

5. The adjustable angle adapter of claim 1, wherein
the inner surface of the opposite end of the guard having a radius that substantially matches a radius of the outer surface of the second portion of the ball receiver.

6. An adjustable angle adapter for a dental tool, comprising:
a nose configured to receive a portion of a dental tool;
a body having two ends, a first end adjustably connected to the nose and a second end opposite the first end, coupled to a power source;
an outer joint including:
a ball portion positioned on the nose,
a ball receiver positioned on the body, the ball receiver comprising a first portion and a second portion, the first portion coupled to the first end of the body, the second portion attachable to the first portion; and,
a guard with an edge of one end of the guard resting against a lip of the nose and an inner surface of an opposite end of the guard resting on an outer surface of the second portion of the ball receiver, the inner surface of the guard being concave, the lip of the nose configured to prevent the guard from moving toward the dental tool, wherein the nose is configured to pivot relative to the body into at least a first configuration and a second configuration as the guard moves along the outer surface of the second portion of the ball receiver.

7. The adjustable angle adapter of claim 6, wherein
in the first configuration, the nose and the body share a common centerline; and
in the second configuration, a centerline of the body is at a non-zero degree angle to a centerline of the nose.

8. The adjustable angle adapter of claim 6, further comprising
a rotating member disposed within the nose,
a shaft disposed within the body, and
a multi-axis rotation joint connecting the shaft to the rotating member, wherein
the multi-axis rotation joint and the outer joint pivot about a common pivot point.

9. The adjustable angle adapter of claim 6, wherein
the nose is configured to pivot relative to the body from between zero degrees to about eighteen degrees.

10. The adjustable angle adapter of claim 6, wherein
the inner surface of the opposite end of the guard having a radius that substantially matches a radius of the outer surface of the second portion of the ball receiver.

11. An adjustable angle adapter for a prophy angle, comprising:
a nose configured to receive a portion of a prophy angle;
a body having two ends, a first end adjustably connected to the nose and a second end opposite the first end, coupled to a power source;
an outer joint including:
a ball portion positioned on the nose,
a ball receiver positioned on the body, the ball receiver comprising a first portion and a second portion, the first portion coupled to the first end of the body, the second portion attachable to the first portion; and,
a guard with an inner surface of one end of the guard resting on a neck of a ball portion and the inner surface of an opposite end of the guard resting on an outer surface of the second portion of the ball receiver, the inner surface of the opposite end of the guard being concave, wherein
the nose is configured to pivot relative to the body into at least a first configuration and a second configuration as the guard moves along the outer surface of the second portion of the ball receiver.

* * * * *

UNITED STATES PATENT AND TRADEMARK OFFICE
CERTIFICATE OF CORRECTION

PATENT NO. : 8,834,159 B2
APPLICATION NO. : 12/712993
DATED : September 16, 2014
INVENTOR(S) : Chris J. Carron and David G. Grither Page 1 of 1

It is certified that error appears in the above-identified patent and that said Letters Patent is hereby corrected as shown below:

In the Specification

- at column 5, line 52, remove the "s" in the word "includes" so to read "the outer joint 300 can also include a stop"

- at column 5, line 56, replace the "a" with "an" so to read "(e.g., an angled surface 313"

- at column 8, lines 25-26, add reference to U.S. Patent No. 8,123,523, so to read "U.S. patent application Ser. No. 11/862,628, filed on Sep. 27, 2007, now U.S. Patent No. 8,123,523, which"

- at column 8, line 55-56, replace the "an" with "a" so to read "a retracted position"

- at column 9, line 55, remove the "a" so to read "is configured as"

- at column 9, line 56, add a "s" on the word "type" so to read "other types of connections"

- at column 9, line 66, add a "s" to "configuration" so to read "many different configurations"

- at column 11, line 13, replace the "is" with "in" so to read "collet bore 208 in this manner"

- at column 12, line 27, replace the word "ration" with the word "ratio" so to read "the range or ratio"

- at column 12, line 47, replace the "an" with "a" so to read "a micromotor 528"

Signed and Sealed this
Second Day of June, 2015

Michelle K. Lee
*Director of the United States Patent and Trademark Office*